Figure 1:
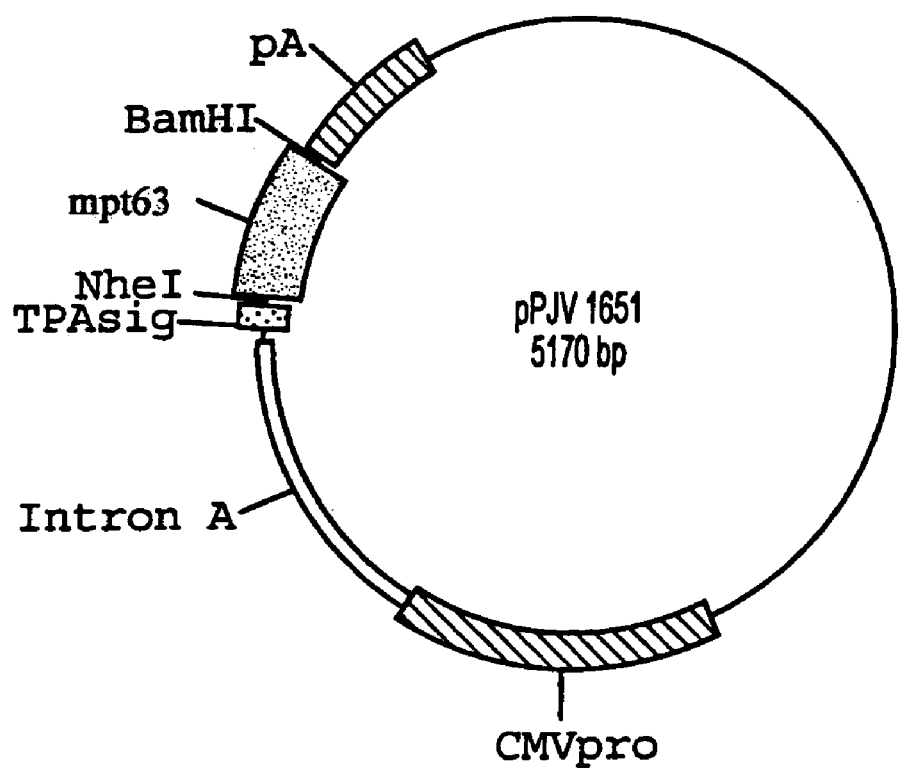

US007022320B1

(12) United States Patent
Macklin et al.

(10) Patent No.: US 7,022,320 B1
(45) Date of Patent: Apr. 4, 2006

(54) ***MYCOBACTERIUM TUBERCULOSIS* IMMUNIZATION**

(75) Inventors: Michael D. Macklin, Madison, WI (US); Deborah L. Fuller, Madison, WI (US)

(73) Assignee: PowderJect Vaccines, Inc., Wilmington, DE (US)

( * ) Notice: Subject to any disclaimer, the term of this patent is extended or adjusted under 35 U.S.C. 154(b) by 0 days.

(21) Appl. No.: 09/501,328

(22) Filed: Feb. 9, 2000

Related U.S. Application Data

(60) Provisional application No. 60/119,515, filed on Feb. 9, 1999, provisional application No. 60/161,699, filed on Oct. 26, 1999.

(51) Int. Cl.

| | |
|---|---|
| *A61K 48/00* | (2006.01) |
| *A61K 39/04* | (2006.01) |
| *C07H 21/02* | (2006.01) |
| *C07H 21/04* | (2006.01) |

(52) U.S. Cl. ................ 424/93.2; 424/248.1; 435/69.1; 435/243; 435/253.1; 435/320.1; 435/863; 514/44; 530/350; 536/23.1; 536/23.7

(58) Field of Classification Search .............. 424/93.2, 424/248.1; 435/69.1, 243, 253.1, 320.1, 435/863; 514/44; 530/350; 536/23.1, 23.7

See application file for complete search history.

(56) References Cited

U.S. PATENT DOCUMENTS

| | | | |
|---|---|---|---|
| 4,629,782 A | 12/1986 | Chan et al. | |
| 4,945,050 A | 7/1990 | Sanford et al. | |
| 4,980,286 A | 12/1990 | Morgan et al. | |
| 4,981,782 A | 1/1991 | Judd et al. | |
| 5,036,006 A | 7/1991 | Sanford et al. | |
| 5,091,188 A | 2/1992 | Haynes | |
| 5,100,792 A | 3/1992 | Sanford et al. | |
| 5,120,657 A | 6/1992 | McCabe et al. | |
| 5,149,655 A | 9/1992 | McCabe | |
| 5,179,022 A | 1/1993 | Sanford et al. | |
| 5,204,253 A | 4/1993 | Sanford | |
| 5,330,754 A * | 7/1994 | Kapoor et al. | 424/190.1 |
| 5,371,015 A | 12/1994 | Sanford et al. | |
| 5,478,744 A | 12/1995 | Sanford et al. | |
| 5,504,005 A * | 4/1996 | Bloom et al. | 435/253.1 |
| 5,584,807 A | 12/1996 | McCabe | |
| 5,589,466 A | 12/1996 | Felgner et al. | |
| 5,591,632 A * | 1/1997 | O'Donnell et al. | 435/252.3 |
| 5,630,796 A * | 5/1997 | Bellhouse et al. | 604/49 |
| 5,658,892 A | 8/1997 | Bellhouse et al. | |
| 5,731,151 A * | 3/1998 | King et al. | 435/6 |
| 5,738,852 A | 4/1998 | Robinson et al. | |
| 5,750,384 A * | 5/1998 | Jacobs et al. | 435/172.3 |
| 5,773,267 A * | 6/1998 | Jacobs et al. | 435/172.1 |
| 5,776,465 A * | 7/1998 | O'Donnell et al. | 424/200.1 |
| 5,854,055 A * | 12/1998 | Bloom et al. | 435/253.1 |
| 5,865,796 A * | 2/1999 | McCabe et al. | 604/71 |
| 5,899,880 A | 5/1999 | Bellhouse et al. | |
| 6,004,286 A | 12/1999 | Bellhouse et al. | |
| 6,010,478 A | 1/2000 | Bellhouse et al. | |
| 6,013,050 A | 1/2000 | Bellhouse et al. | |
| 6,168,587 B1 | 1/2001 | Bellhouse et al. | |
| 6,194,389 B1 | 2/2001 | Johnston et al. | |

FOREIGN PATENT DOCUMENTS

| | | |
|---|---|---|
| EP | 0213894 A3 | 3/1987 |
| EP | 0390435 A | 10/1990 |
| WO | WO 89/05349 | 6/1989 |
| WO | WO 90/01949 | 3/1990 |
| WO | WO 91/00359 | 1/1991 |
| WO | WO 91/07487 | 5/1991 |
| WO | WO 93/19183 | 9/1993 |
| WO | WO 94/09819 | 5/1994 |
| WO | WO 94/21797 | 9/1994 |
| WO | WO 94/24263 | 10/1994 |
| WO | WO 95/19799 | 7/1995 |
| WO | WO 95/20660 | 8/1995 |
| WO | WO 96/04947 | 2/1996 |
| WO | WO 96/12513 | 5/1996 |
| WO | WO 96/14855 | 5/1996 |
| WO | WO 96/15241 | 5/1996 |
| WO | WO 96/20022 | 7/1996 |
| WO | WO 97/32987 | 9/1997 |
| WO | WO 97/40163 | 10/1997 |
| WO | WO 97/48485 | 12/1997 |
| WO | WO 98/10750 | 3/1998 |
| WO | WO 98/46263 | 10/1998 |
| WO | WO 99/27961 | 6/1999 |
| WO | WO 00/12121 | 3/2000 |
| WO | WO 00/13704 | 3/2000 |

OTHER PUBLICATIONS

Morris et al, The Immunogenicity of single and combination DNA vaccines against tuberculosis, Vaccine, vol. 18, pp. 2155-2163, 2000.*

(Continued)

*Primary Examiner*—Rodney P Swartz

(74) *Attorney, Agent, or Firm*—Foley & Lardner LLP

(57) ABSTRACT

Recombinant nucleic acid molecules are described. The molecules have a sequence or sequences encoding at least two *M. tuberculosis* antigens. Vectors and compositions containing these molecules are also described. In addition, compositions containing a cocktail of recombinant nucleic acid molecules having a sequence or sequences encoding one or more *M. tuberculosis* antigens are described. Methods of eliciting an immune response using these molecules and compositions are also described.

33 Claims, 20 Drawing Sheets

OTHER PUBLICATIONS

Lowrie et al, Protection against tuberculosis by a plasmid DNA vaccine, Vaccine, vol. 15, No. 8, pp. 834-838, 1997.*
Remington's Pharmaceutical Sciences (1980) Mark Publishing Company, Pennsylvania, pp1483-1484 and 1535.
Townsend et al. (1984) *Cell 39*:13.
Townsend et al. (1985) *Prog. Allergy 36*:10.
Sanford et al. (1987) "Delivery of substances into cells and tissues using a particle bombardment process," *Particulate Science and Technology 5*:27-37.
Klein et al (1987) "High velocity microprojectiles for delivering nucleic acids into living cells," *Nature 327*:7-73.
Tang et al. (1988) *J. Virology 62*:4745-4751.
Zelenin et al. (1989) "Genetic transformation of mouse cultured cells with the help of high-velocity mechanical DNA injection," *FEBS Letters 244*:65-67.
Milich (1989) *Advances in Immunology 45*:195.
S.A. Johnston (1990) "Biolistic transformation: microbes to mice," *Nature 346*:776-777.
Poznansky et al. (1991) *J. Virology 65*:532-536.
Haynes et al. (1991) *Mol. Immunology 28*:231-234.
Rhim et al. (1991) *J. Virology 65*:4555-4564.
Rousseaux-Prevost et al. (1991) *Molecular Immunology 28*:943-949.
Haynes et al. (1994) *Aides Res. and Human Retroviruses 10*(suppl..2):S43-S45.
Sedegah et al. (1994) *Proc. Natl. Acad. Sci. USA 91*:9866-9870.
Fynan et al. (1995) *Int. J. Immunopharmac. 17*:79-83.
Sarphie et al. (1997) *J. Controlled Release 47*:61-69.
Morris et al. (2000) *Vaccine 18*:2155-2163.

* cited by examiner

SEQUENCE LISTING

```
<160> NUMBER OF SEQ ID NOS:  20

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:   Antigen
      85A forward primer

<400> SEQUENCE: 1
ggagctagcg cattttcccg gccgggcttg                                           30

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Antigen 85A
      reverse primer

<400> SEQUENCE: 2
ggtggatccc taggcgccct ggggcgc                                              27
```

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Antigen 85B
      forward primer

<400> SEQUENCE: 3
ggagctagct tctcccggcc ggggctg                                        27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Antigen 85B
      reverse primer

<400> SEQUENCE: 4
ggtggatcct cagccggcgc ctaacga                                        27

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Antigen 85C
      forward primer

<400> SEQUENCE: 5
ggagctagct tctctaggcc cggtctt                                        27

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Antigen 85C
      reverse primer

<400> SEQUENCE: 6
ggtggatcct caggcggccg gcgcagc                                        27

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: ESAT-6
      forward primer

<400> SEQUENCE: 7
ggagctagca tgacagagca gcagtggaat                                     30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: ESAT-6
      reverse primer

<400> SEQUENCE: 8
ggtggatccc tatgcgaaca tcccagtgac                                     30

```
<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: DES
      forward primer

<400> SEQUENCE: 9
ggagctagca tgtcagccaa gctgaccga                                29

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: DES
      reverse primer

<400> SEQUENCE: 10
ggtggatccc taacgacggc tcatcgccag                               30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: MPT 51
      forward primer

<400> SEQUENCE: 11
ggagctagcg ccccatacga gaacctgatg                               30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: MPT 51
      reverse primer

<400> SEQUENCE: 12
cctggatcct tagcggatcg caccgacgat                               30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: MPT 32
      (45/47 gene) forward primer

<400> SEQUENCE: 13
ggagctagcg atccggagcc agcgcccccg                               30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: MPT 32
      (45/47 gene) reverse primer

<400> SEQUENCE: 14
cctggatcct caggccggta aggtccgctg                               30

<210> SEQ ID NO 15
```

```
<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: MPT 64
      forward primer

<400> SEQUENCE: 15
ggagctagcg cgcccaagac ctactgcgag                                          30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: MPT 64
      reverse primer

<400> SEQUENCE: 16
cctggatccc taggccagca tcgagtcgat                                          30

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: MPT 63
      forward primer

<400> SEQUENCE: 17
gggctagcgc ctatcccatc accggaaaac ttggcagtga                               40

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: MPT 63
      reverse primer

<400> SEQUENCE: 18
ggatccctac ggctcccaaa tcagcagatc ctccat                                   36

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: hsp65
      forward primer

<400> SEQUENCE: 19
ggagctagca tggccaagac aattgcgtac                                          30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: hsp65
      reverse primer

<400> SEQUENCE: 20
cctggatcct cagaaatcca tgccacccat                                          30
```

MYCOBACTERIUM TUBERCULOSIS IMMUNIZATION

CROSS-REFERENCE TO RELATED APPLICATIONS

This application is related to provisional patent applications Ser. Nos. 60/119,515, filed Feb. 9, 1999 and 60/161,699, filed Oct. 26, 1999, from which priority is claimed under 35 USC §119(e)(1) and which applications are incorporated herein by reference in their entireties.

TECHNICAL FIELD

The invention relates to the fields of molecular biology and immunology, and generally relates to nucleic acid immunization techniques. More specifically, the invention relates to polynucleotides encoding at least two *M. tuberculosis* antigens, and to nucleic acid immunization strategies employing such polynucleotides.

BACKGROUND

Techniques for the injection of DNA and mRNA into mammalian tissue for the purposes of immunization against an expression product have been described in the art. The techniques, termed "nucleic acid immunization" herein, have been shown to elicit both humoral and cell-mediated immune responses. For example, sera from mice immunized with a DNA construct encoding the envelope glycoprotein, gp160, were shown to react with recombinant gp160 in immunoassays, and lymphocytes from the injected mice were shown to proliferate in response to recombinant gp120. Wang et al. (1993) *Proc. Natl. Acad. Sci. USA* 90:4156–4160. Similarly, mice immunized with a human growth hormone (hGH) gene demonstrated an antibody-based immune response. Tang et al. (1992) *Nature* 356:152–154. Intramuscular injection of DNA encoding influenza nucleoprotein driven by a mammalian promoter has been shown to elicit a CD8+ CTL response that can protect mice against subsequent lethal challenge with virus. Ulmer et al. (1993) *Science* 259:1745–1749. Immunohistochemical studies of the injection site revealed that the DNA was taken up by myeloblasts, and cytoplasmic production of viral protein could be demonstrated for at least 6 months.

The genus *Mycobacterium* includes at least 54 species (Wayne et al. (1986) Genus *Mycobacterium* in "Bergey's Manual of Systematic Bacteriology," Sneath et al. eds., Vol. 2, pp. 1436–1457, Williams & Wilkins, Baltimore, Md.). Most of these species are saprophytes and do not cause human or animal diseases. The medically relevant mycobacteria (i.e., relevant in terms of morbidity and mortality in man) are *Mycobacterium tuberculosis* (*M. tuberculosis*) and *M. leprae*, which cause tuberculosis and leprosy, respectively. Tuberculosis is currently the leading worldwide cause of human mortality from infectious disease and is predicted to be responsible for upwards of 30 million deaths during the decade spanning the years 1990 to 2000. Raviglione et al. (1995) *JAMA* 273:220–226.

Currently, human tuberculosis vaccines are made from *M. bovis* bacillus Calmette-Guerin ("*M. bovis*-BCG" or "BCG") (Calmette et al. (1924) *Bull. Acad. Natl. Med.* 91:787–796). With nearly 2 billion immunizations, BCG has a long record of safe use in people (Luelmo (1982) *Am. Rev. Respir. Dis.* 125:70–72 and Lotte et al. (1984) *Adv. Tuberc. Res.* 21:107–193). It can be given at birth and a single dose provides long-term protection. However, because the protective efficacy of the BCG vaccine has varied between 0% and 80% across various populations and geographic regions, efforts to develop new vaccines are needed. Rodrigues et al. (1990) *Trans. R. Soc. Trop. Med. Hyg.* 84:739–744; World Health Organization (1979) *Bull. W.H.O.* 57:810–827.

The genes encoding various immunogenic *M. tuberculosis* proteins have been sequenced, for example the antigen 85 complex of proteins (85A, 85B, 85C) (Wiker and Harboe, (1992) *Microbiol. Rev.* 56:648); ESAT-6 (Andersen (1994) *Infect. Immunity* 62:2536); Des (Jackson et al. (1997) *Infect. & Immunity* 65:2883–2889); 45/47 kDa (also known as MPT 32) secreted protein(s) (Borremans et al. (1989) *Infect. Immun.* 57(10):3123–3130 and U.S. Pat. No. 5,714,593); MPT 51 (NCBI # AJ002150); MPT 64 (Oettinger and Andersen (1994) *Infect. Immun.* 62(5) 2058–2064; MPT63 and hsp 65.

U.S. Pat. No. 5,736,524 describes attempts to prepare a vaccine for tuberculosis comprising a DNA molecule which encodes a mature antigen 85A protein. International Publication WO 96/31613 describes expression library immunization (ELI) which involves introducing vectors carrying fragments of genomic DNA from *Mycoplasma* or *Listeria* to elicit an immune response. Selected pools are then identified and further characterized in order to develop new vaccines based on novel epitopes.

However, there remains a need for more effective vaccines and methods of immunization against *tuberculosis*.

SUMMARY OF THE INVENTION

It is a primary object of the invention to provide a composition containing recombinant nucleic acid molecules which encode at least two *M. tuberculosis* antigens. The composition is used as a reagent in various nucleic acid immunization strategies. In one particular embodiment of the invention, a cocktail of recombinant nucleic acid molecules is provided, each molecule having a sequence encoding a different *M. tuberculosis* antigen. In a related embodiment, the cocktail includes one or more polynucleotides encoding two or more *M. tuberculosis* antigens. In another particular embodiment, at least two *M. tuberculosis* antigens are encoded by a single polynucleotide. The *M. tuberculosis* antigens encoded by the nucleic acid sequences can be any suitable *M. tuberculosis* antigen, preferably antigens such as the 65 kD heat shock protein (HSP65) of *M. tuberculosis*, or a major culture filtrate protein antigen of *M. tuberculosis* such as, for example, Antigen 85A, Antigen 85B, Antigen 85C, ESAT-6, Des Protein, MPT32, MPT51, MPT63 and MPT64.

It is also a primary object of the invention to provide a method for eliciting an immune response against one or more *M. tuberculosis* antigens of interest in an immunized subject. The method entails a primary immunization step comprising one or more steps of transfecting cells of the subject with a composition containing recombinant nucleic acid molecules encoding at least two *M. tuberculosis* antigens. Expression cassettes and/or vectors containing any one of the recombinant nucleic acid molecules of the present invention can be used to transfect the cells, and transfection is carried out under conditions that permit expression of the antigens within the subject. The method may further entail a secondary, or booster immunization step comprising one or more steps of administering at least one secondary composition to the subject. In one embodiment, the secondary composition comprises, or contains sequences encoding the same *M. tuberculosis* antigens. In another embodiment, the secondary composition is a protein antigen, for instance, culture filtrate proteins from *M. tuberculosis*. In yet another embodiment, the secondary composition is an attenuated live vaccine, for example, BCG. Either the primary, or the combination of the primary and secondary immunization steps is sufficient to elicit a robust immune response against the *M. tuberculosis* agent.

The transfection procedure carried out during the primary immunization step can be conducted either in vivo, or ex vivo (e.g., to obtain transfected cells which are subsequently introduced into the subject prior to carrying out the secondary immunization step). When in vivo transfection is used, the recombinant nucleic acid molecules can be administered to the subject by way of intramuscular or intradermal injection of plasmid DNA or, preferably, administered to the subject using a particle-mediated delivery technique. The secondary composition can include the antigens of interest in the form of any suitable vaccine composition, for example, in the form of a peptide subunit composition, in the form of a nucleic acid vaccine composition, or in the form of a recombinant viral vector which contains the relevant coding sequences for the *M. tuberculosis* antigens of interest. Preferably, the secondary composition comprises BCG, for example in the form of a bacterial vector.

Advantages of the present invention include, but are not limited to: (i) providing recombinant polynucleotides encoding a plurality of *M. tuberculosis* antigens; (ii) use of these polynucleotides as reagents in nucleic acid immunization strategies to attain an immune response against *M. tuberculosis*; (ii) use of these polynucleotides in combination with secondary compositions (e.g., BCG) to elicit an enhanced (e.g., synergistic) immune response against *M. tuberculosis*.

These and other objects, aspects, embodiments and advantages of the present invention will readily occur to those of ordinary skill in the art in view of the disclosure herein.

BRIEF DESCRIPTION OF THE DRAWINGS

FIG. 1 is a schematic depiction of plasmid PJV1651 which encodes the MPT63 gene product.

FIG. 2 is a schematic depiction of plasmid PJV1652 which encodes the DES gene product.

FIG. 3 is a schematic depiction of plasmid PJV1653 which encodes the ESAT-6 gene product.

FIG. 4 is a schematic depiction of plasmid PJV1654 which encodes the 85A gene product.

FIG. 5 is a schematic depiction of plasmid PJV1655 which encodes the 85B gene product.

FIG. 6 is a schematic depiction of plasmid PJV1657 which encodes the 85C gene product.

FIG. 7 is a schematic depiction of plasmid PJV1658 which encodes the MPT32 gene product.

FIG. 8 is a schematic depiction of plasmid PJV1659 which encodes the MPT64 gene product.

FIG. 9 is a schematic depiction of plasmid PJV1660 which encodes the MPT51 gene product.

FIG. 10 is a schematic depiction of plasmid PJV1661 which encodes the hsp65 gene product.

FIG. 11, panels A and B depict *M. tuberculosis* colony forming units (CFUs) in guinea pigs five weeks post-challenge. Each bar corresponds to a different Group of animals. The treatment regime for each Group is described in detail in the Examples. Each symbol represents an individual test guinea pig. FIG. 11A depicts CFUs in lung. FIG. 11B depicts CFUs in spleen.

FIG. 12, panels A–F, depict survival data for guinea pigs challenged with *M. tuberculosis*. Each panel depicts each animal of the group separately. Panel A depicts survival of guinea pigs (animals 411, 420, 436 and 445) immunized with the antigen 85A. Panel B depicts survival of guinea pigs (animals 408, 423, 431, 449, 455) immunized with antigen 85A and MPT32. Panel C depicts survival of guinea pigs (animals 409, 421, 434, 440 and 460) immunized with a cocktail of antigens including 85A, 85B, 85C, MPT32, MPT51, MPT63, MPT64, Des, ESAT-6 and hps65. Panel D depicts survival of guinea pigs (animals 406, 418, 429, 437, 448) immunized with a cocktail of antigens including 85A, 85B, 85C, MPT32, MPT51, MPT63, MPT64, Des, ESAT-6, hps65 and boosted with BCG. Panel E depicts survival of a negative control animals (402, 414, 425, 443 and 452). Panel F depicts survival of guinea pigs immunized with BCG alone.

FIG. 13 depicts histopathology scores of tissue obtained from guinea pigs challenged with *tuberculosis*. FIG. 13A depicts lung tissue and FIG. 13B depicts spleen tissue.

DETAILED DESCRIPTION OF THE INVENTION

Before describing the present invention in detail, it is to be understood that this invention is not limited to particularly exemplified molecules or process parameters as such may, of course, vary. It is also to be understood that the terminology used herein is for the purpose of describing particular embodiments of the invention only, and is not intended to be limiting. In addition, the practice of the present invention will employ, unless otherwise indicated, conventional methods of virology, microbiology, molecular biology, recombinant DNA techniques and immunology all of which are within the ordinary skill of the art. Such techniques are explained fully in the literature. See, e.g., Sambrook, et al., *Molecular Cloning: A Laboratory Manual* (2nd Edition, 1989); *DNA Cloning: A Practical Approach*, vol. I & II (D. Glover, ed.); *Oligonucleotide Synthesis* (N. Gait, ed., 1984); *A Practical Guide to Molecular Cloning* (1984); and *Fundamental Virology,* 2nd Edition, vol. I & II (B. N. Fields and D. M. Knipe, eds.).

All publications, patents and patent applications cited herein, whether supra or infra, are hereby incorporated by reference in their entirety.

It must be noted that, as used in this specification and the appended claims, the singular forms "a," "an" and "the" include plural referents unless the content clearly dictates otherwise.

Definitions

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed, and are intended to be defined as indicated below.

The term "nucleic acid immunization" is used herein to refer to the introduction of a nucleic acid molecule encoding one or more selected antigens into a host cell for the in vivo expression of the antigen or antigens. The nucleic acid molecule can be introduced directly into the recipient subject, such as by standard intramuscular or intradermal injection; transdermal particle delivery; inhalation; topically, or by oral, intranasal or mucosal modes of administration. The molecule alternatively can be introduced ex vivo into cells which have been removed from a subject. In this latter case, cells containing the nucleic acid molecule of interest are re-introduced into the subject such that an immune response can be mounted against the antigen encoded by the nucleic acid molecule.

By "core carrier" is meant a carrier on which a nucleic acid (e.g., DNA) is coated in order to impart a defined particle size as well as a sufficiently high density to achieve the momentum required for cell membrane penetration, such that the DNA can be delivered using particle-mediated techniques, such as by use of a particle-mediated delivery techniques (see, e.g., U.S. Pat. No. 5,100,792). Core carriers typically include materials such as tungsten, gold, platinum, ferrite, polystyrene and latex. See e.g., *Particle Bombardment Technology for Gene Transfer*, (1994) Yang, N. ed., Oxford University Press, New York, N.Y. pages 10–11. By "needleless syringe" is meant an instrument which delivers a particulate composition transdermally, without a conventional needle that pierces the skin. Needleless syringes for use with the present invention are discussed throughout this document.

The term "transdermal" delivery intends intradermal (e.g., into the dermis or epidermis), transdermal (e.g., "percutaneous") and transmucosal administration, i.e., delivery by passage of an agent into or through skin or mucosal tissue. See, e.g., *Transdermal Drug Delivery: Developmental Issues and Research Initiatives*, Hadgraft and Guy (eds.), Marcel Dekker, Inc., (1989); *Controlled Drug Delivery: Fundamentals and Applications*, Robinson and Lee (eds.), Marcel Dekker Inc., (1987); and *Transdermal Delivery of Drugs*, Vols. 1–3, Kydonieus and Berner (eds.), CRC Press, (1987). Thus, the term encompasses delivery from a needleless syringe deliver as described in U.S. Pat. No. 5,630,796, as well as particle-mediated delivery as described in U.S. Pat. No. 5,865,796.

A "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein.

An "antigen" refers to any agent, generally a macromolecule, which can elicit an immunological response in an individual. The term may be used to refer to an individual macromolecule or to a homogeneous or heterogeneous population of antigenic macromolecules. As used herein, "antigen" is generally used to refer to a protein molecule or portion thereof which contains one or more epitopes. For purposes of the present invention, antigens can be obtained or derived from any appropriate source. Furthermore, for purposes of the present invention, an "antigen" includes a protein having modifications, such as deletions, additions and substitutions (generally conservative in nature) to the native sequence, so long as the protein maintains sufficient immunogenicity. These modifications may be deliberate, for example through site-directed mutagenesis, or may be accidental, such as through mutations of hosts which produce the antigens.

By "subunit vaccine" is meant a vaccine composition which includes one or more selected antigens but not all antigens, derived from or homologous to, an antigen from a pathogen of interest such as from a virus, bacterium, parasite or fungus. Such a composition is substantially free of intact pathogen cells or pathogenic particles, or the lysate of such cells or particles. Thus, a "subunit vaccine" can be prepared from at least partially purified (preferably substantially purified) immunogenic polypeptides from the pathogen, or analogs thereof. The method of obtaining an antigen included in the subunit vaccine can thus include standard purification techniques, recombinant production, or synthetic production.

A "live attenuated vaccine" is a weakened (e.g., by genetic modification) bacteria, virus or fractions thereof used to produce active immunity in a subject. An example of a live attenuated vaccine is BCG, as described above.

An "immune response" against an antigen of interest is the development in an individual of a humoral and/or a cellular immune response to that antigen. For purposes of the present invention, a "humoral immune response" refers to an immune response mediated by antibody molecules, while a "cellular immune response" is one mediated by T-lymphocytes and/or other white blood cells.

The terms "nucleic acid molecule" and "polynucleotide" are used interchangeably to and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

A "cocktail" refers to a composition containing more than one type of polynucleotide. Thus, in the context of the present invention, a cocktail includes at least two polynucleotides encoding different *M. tuberculosis* antigens. As described herein, the combinations of polynucleotides making up the cocktail can be varied. For example, the cocktail of polynucleotides can include polynucleotides encoding at least two, such as a plurality of *M. tuberculosis* antigens or, alternatively, some of the polynucleotides of the cocktail can encode one antigen while others can encode a plurality of antigens. Suitable combinations of polynucleotides useful in cocktails can be readily determined by a skilled artisan in view of the teachings herein.

A "vector" is capable of transferring gene sequences to target cells (e.g., viral vectors, non-viral vectors, particulate carriers, and liposomes). Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as viral vectors. A "plasmid" is an extrachromosomal genetic element.

A "coding sequence," or a sequence which "encodes" a selected antigen, is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, a coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence.

A "promoter" is a nucleotide sequence which initiates and regulates transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" is used herein to describe a nucleic acid molecule (polynucleotide) of genomic, cDNA, semisynthetic, or synthetic origin which, by virtue of its origin or manipulation is not associated with all or a portion of the polynucleotide with which it is associated in nature and/or is linked to a polynucleotide other than that to which it is linked in nature. Two nucleic acid sequences which are contained within a single recombinant nucleic acid molecule are "heterologous" relative to each other when they are not normally associated with each other in nature.

Techniques for determining nucleic acid and amino acid "sequence identity" or "sequence homology" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482–489 (1981). This algorithm can be applied to amino acid sequences by using the scoring matrix developed by Dayhoff, *Atlas of Protein Sequences and Structure*, M. O. Dayhoff ed., 5 suppl. 3:353–358, National Biomedical Research Foundation, Washington, D.C., USA, and normalized by Gribskov, *Nucl. Acids Res.* 14(6):6745–6763 (1986).

An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%–85%, preferably at least about 90%, and most preferably at least about 95%–98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. For example, stringent hybridization conditions can include 50% formamide, 5× Denhardt's Solution, 5×SSC, 0.1% SDS and 100 µg/ml denatured salmon sperm DNA and the washing conditions can include 2×SSC, 0.1% SDS at 37° C. followed by 1×SSC, 0.1% SDS at 68° C. Defining appropriate hybridization conditions is within the skill of the art. See, e.g., Sambrook et al., supra; *DNA Cloning*, supra; *Nucleic Acid Hybridization*, supra.

As used herein the term "adjuvant" refers to any material that facilitates or enhances the immune response to a drug, antigen, polynucleotide, vector or the like. It is intended, although not always explicitly stated, that molecules having similar biological activity as wild-type or purified peptide adjuvants (e.g., recombinantly produced or muteins thereof) and nucleic acid encoding these molecules are intended to be used within the spirit and scope of the invention.

The terms "individual" and "subject" are used interchangeably herein to refer to any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms do not denote a particular age. Thus, both adult and newborn individuals are intended to be covered. The methods described herein are intended for use in any of the above vertebrate species, since the immune systems of all of these vertebrates operate similarly.

General Overview

The present invention provides novel polynucleotides and vectors comprising M. tuberculosis antigens. These molecules are useful in eliciting an immune response in a subject against M. tuberculosis. In particular, the present inventors have determined that administration of nucleic acid immunization, for example using particle-mediated delivery techniques to administer core carriers coated with the polynucleotide encoding a M. tuberculosis antigen, results in greater than a 10-fold reduction in guinea pig spleen M. tuberculosis counts as compared to intramuscular immunization of the polynucleotide.

The present inventors have also determined that using the nucleic acid immunization techniques described herein as a priming immunization and BCG as a booster immunization provides substantially enhanced protection as compared to (1) BCG alone; (2) BCG prime with BCG boost; and (3) nucleic acid (single or combination) immunization. Thus, the invention provides more effective vaccines and methods of immunization against infection with M. tuberculosis.

Polynucleotides

In one embodiment, a recombinant nucleic acid vaccine composition is provided. The composition includes one or more recombinant polynucleotides encoding at least two M. tuberculosis antigens. In one particular embodiment, a cocktail of nucleic acid molecules is provided, each molecule having a sequence encoding a M. tuberculosis antigen. In a related embodiment, the cocktail includes one or more polynucleotides encoding two or more M. tuberculosis antigens. In another particular embodiment, at least two M. tuberculosis antigens are encoded on one polynucleotide.

The entire M. tuberculosis genome has been sequenced and the sequences are publically available, for example on the World Wide Web. In particular, M. tuberculosis antigens encoded by these known nucleic acid sequences can be any suitable M. tuberculosis antigen, and will preferably be well characterized and highly immunogenic antigens such as the 65 kD heat shock protein (HSP65) of M. tuberculosis, or a major culture filtrate protein of M. tuberculosis such as, for example, Antigen 85A, Antigen 85B, Antigen 85C, ESAT-6, Des Protein, MPT32, MPT51, MPT63, and MPT64 (see, e.g., Andersen, P. (1994) Infect. Immun. 62:2536–2544; Belisle et al. (1997) Science 276:1420–1422; Horwitz et al. (1995) Proc. Natl. Acad. Sci. USA 92:1530–1534; Hubbard et al. (1992) Clin. Exp. Immunol. 87:94–98; Huygen et al. (1996) Nat. Med. 2:893–898; Pal et al. (1992) Infect. Immun. 60:4781–4792; and Roberts et al. (1995) Immunology 85:502–508). Active variants of these antigens may also be used in the subject compositions and methods. Sequences encoding the selected M. tuberculosis antigens are typically inserted into an appropriate vector (e.g., plasmid) backbone using known techniques and as described below in the Examples.

The M. tuberculosis portion of these recombinant nucleic acid molecules can be obtained from known sources. In this regard, the M. tuberculosis species is comprised of a single homogeneous serotype that is divisible into three major and one intermediate phage types (A, B, C, and I, respectively) based upon susceptibility to bacteriophage lysis. The sequences of major antigenic portions of the M. tuberculosis genome are known and generally well characterized. For example, sequences for the 65 kD antigen of M. tuberculosis have been disclosed in International Publication Nos. WO 88/06591 and WO 90/12875. Sequences for major culture filtrate protein antigens of M. tuberculosis (Antigen 85A, Antigen 85B, Antigen 85C, ESAT-6, Des Protein, MPT32, MPT51, MPT63, and MPT64) are also disclosed or publically available (see, e.g., Andersen, P. (1994) Infect. Immun. 62:2536–2544; Belisle et al. (1997) Science 276:1420–1422; Horwitz et al. (1995) Proc. Natl. Acad. Sci. USA 92:1530–1534; Hubbard et al. (1992) Clin. Exp. Immunol. 87:94–98; Huygen et al. (1996) Nat. Med. 2:893–898; Pal et al. (1992) Infect. Immun. 60:4781–4792; and Roberts et al. (1995) Immunology 85:502–508). Recombinant DNA libraries containing genomic fragments of M. tuberculosis are known and are publically available, for example the recombinant expression library described by Young et al. (1985) Proc. Natl. Acad. Sci. USA 82:2583–2587.

The sequence or sequences encoding the M. tuberculosis antigens of interest can be obtained and/or prepared using known methods. For example, substantially pure antigen preparations can be obtained using standard molecular biological tools. That is, polynucleotide sequences coding for the above-described antigens can be obtained using recombinant methods, such as by screening cDNA and genomic libraries from cells expressing an antigen, or by deriving the coding sequence for the M. tuberculosis antigen from a vector known to include the same. Furthermore, the desired sequences can be isolated directly from cells and tissues containing the same, using standard techniques, such as phenol extraction and PCR of cDNA or genomic DNA. See, e.g., Sambrook et al., supra, for a description of techniques used to obtain and isolate DNA. Polynucleotide sequences can also be produced synthetically, rather than cloned.

Yet another convenient method for isolating specific nucleic acid molecules is by the polymerase chain reaction (PCR). Mullis et al. (1987) Methods Enzymol. 155:335–350. This technique uses DNA polymerase, usually a thermostable DNA polymerase, to replicate a desired region of DNA. The region of DNA to be replicated is identified by oligonucleotides of specified sequence complementary to opposite ends and opposite strands of the desired DNA to prime the replication reaction. The product of the first round of replication is itself a template for subsequent replication, thus repeated successive cycles of replication result in geometric amplification of the DNA fragment delimited by the primer pair used.

Once the sequences for the M. tuberculosis antigens of interest have been obtained, they can be linked together to provide one or more contiguous nucleic acid molecules using standard cloning or molecular biology techniques. More particularly, after the sequence information for the M. tuberculosis antigens of interest has been obtained, they can be combined to form a hybrid sequence, or handled separately. In hybrid sequences, the various antigen sequences can be positioned in any manner relative to each other, and be included in a single molecule in any number ways, for example, as a single copy, randomly repeated in the molecule as multiple copies, or included in the molecule as multiple tandem repeats or otherwise ordered repeat motifs.

Although any number of routine molecular biology techniques can be used to construct such recombinant nucleic acid molecules, one convenient method entails using one or more unique restriction sites in a shuttle or cloning vector (or inserting one or more unique restriction sites into a suitable vector sequence) and standard cloning techniques to direct the *M. tuberculosis* antigen sequence or sequences to particular target locations within a vector sequence.

Alternatively, hybrid molecules can be produced synthetically rather than cloned. The nucleotide sequence can be designed with the appropriate codons for the particular amino acid sequence desired. In general, one will select preferred codons for the intended host in which the sequence will be expressed. The complete sequence can then be assembled from overlapping oligonucleotides prepared by standard methods and assembled into a complete coding sequence. See, e.g., Edge (1981) *Nature* 292:756; Nambair et al. (1984) *Science* (1984) 223:1299; Jay et al. (1984) *J. Biol. Chem.* 259:6311.

Once the individual *M. tuberculosis* antigen sequences, and/or hybrid *M. tuberculosis* antigen sequences have been obtained or constructed, they can be inserted into a vector which includes control sequences operably linked to the inserted sequence or sequences, thus allowing for expression of the *M. tuberculosis* antigens in vivo in a targeted subject species.

Typical promoters for mammalian cell expression include the SV40 early promoter, a CMV promoter such as the CMV immediate early promoter, the mouse mammary tumor virus LTR promoter, the adenovirus major late promoter (Ad MLP), and other suitably efficient promoter systems. Non-viral promoters, such as a promoter derived from the murine metallothionein gene, may also be used for mammalian expression. Inducible, repressible or otherwise controllable promoters may also be used. Typically, transcription termination and polyadenylation sequences will also be present, located 3' to each translation stop codon. Preferably, a sequence for optimization of initiation of translation, located 5' to each coding sequence, is also present. Examples of transcription terminator/polyadenylation signals include those derived from SV40, as described in Sambrook et al., supra, as well as a bovine growth hormone terminator sequence. Introns, containing splice donor and acceptor sites, may also be designed into the expression cassette.

In addition, enhancer elements may be included within the expression cassettes in order to increase expression levels. Examples of suitable enhancers include the SV40 early gene enhancer (Dijkema et al. (1985) *EMBO J.* 4:761), the enhancer/promoter derived from the long terminal repeat (LTR) of the Rous Sarcoma Virus (Gorman et al. (1982) *Proc. Natl. Acad. Sci. USA* 79:6777), and elements derived from human or murine CMV (Boshart et al. (1985) *Cell* 41:521), for example, elements included in the CMV intron A sequence.

Administration of Polynucleotides

Once complete, these constructs are used for nucleic acid immunization using standard gene delivery protocols. Methods for gene delivery are known in the art. See, further below. The nucleic acid molecules of the present invention can thus be delivered either directly to a subject or, alternatively, delivered ex vivo to cells derived from the subject whereafter the cells are reimplanted in the subject.

Viral Vectors

A number of viral based systems have been used for gene delivery. For example, retroviral systems are known and generally employ packaging lines which have an integrated defective provirus (the "helper") that expresses all of the genes of the virus but cannot package its own genome due to a deletion of the packaging signal, known as the psi sequence. Thus, the cell line produces empty viral shells. Producer lines can be derived from the packaging lines which, in addition to the helper, contain a viral vector which includes sequences required in cis for replication and packaging of the virus, known as the long terminal repeats (LTRs). The gene of interest can be inserted in the vector and packaged in the viral shells synthesized by the retroviral helper. The recombinant virus can then be isolated and delivered to a subject. (See, e.g., U.S. Pat. No. 5,219,740.) Representative retroviral vectors include but are not limited to vectors such as the LHL, N2, LNSAL, LSHL and LHL2 vectors described in e.g., U.S. Pat. No. 5,219,740, incorporated herein by reference in its entirety, as well as derivatives of these vectors, such as the modified N2 vector described herein. Retroviral vectors can be constructed using techniques well known in the art. See, e.g., U.S. Pat. No. 5,219,740; Mann et al. (1983) *Cell* 33:153–159.

Adenovirus based systems have been developed for gene delivery and are suitable for delivering the polynucleotides described herein. Human adenoviruses are double-stranded DNA viruses which enter cells by receptor-mediated endocytosis. These viruses are particularly well suited for gene transfer because they are easy to grow and manipulate and they exhibit a broad host range in vivo and in vitro. For example, adenoviruses can infect human cells of hematopoietic, lymphoid and myeloid origin. Furthermore, adenoviruses infect quiescent as well as replicating target cells. Unlike retroviruses which integrate into the host genome, adenoviruses persist extrachromosomally thus minimizing the risks associated with insertional mutagenesis. The virus is easily produced at high titers and is stable so that it can be purified and stored. Even in the replication-competent form, adenoviruses cause only low level morbidity and are not associated with human malignancies. Accordingly, adenovirus vectors have been developed which make use of these advantages. For a description of adenovirus vectors and their uses see, e.g., Haj-Ahmad and Graham (1986) *J. Virol.* 57:267–274; Bett et al. (1993) *J. Virol.* 67:5911–5921; Mittereder et al. (1994) *Human Gene Therapy* 5:717–729; Seth et al. (1994) *J. Virol.* 68:933–940; Barr et al. (1994) *Gene Therapy* 1:51–58; Berkner, K. L. (1988) *BioTechniques* 6:616–629; Rich et al. (1993) *Human Gene Therapy* 4:461–476.

Adeno-associated viral vector (AAV) can also be used to administer the polynucleotides described herein. AAV vectors can be derived from any AAV serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes, but retain one or more functional flanking inverted terminal repeat (ITR) sequences. Functional ITR sequences are necessary for the rescue, replication and packaging of the AAV virion. Thus, an AAV vector includes at least those sequences required in cis for replication and packaging (e.g., functional ITRs) of the virus. The ITR sequence need not be the wild-type nucleotide sequence, and may be altered, e.g., by the insertion, deletion or substitution of nucleotides, so long as the sequence provides for functional rescue, replication and packaging.

AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is bounded (5' and 3') with functional AAV ITR sequences. Suitable AAV constructs can be designed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) *Molec. Cell. Biol.* 8:3988–3996; Vincent et al. (1990) *Vaccines* 90 (Cold Spring Harbor Laboratory Press); Carter, B. J. (1992) *Current Opinion in Biotechnology* 3:533–539; Muzyczka, N. (1992) *Current Topics in Microbiol. and Immunol.* 158:97–129; Kotin, R. M. (1994) *Human Gene Therapy* 5:793–801; Shelling and Smith (1994) *Gene Therapy* 1:165–169; and Zhou et al. (1994) *J. Exp. Med.* 179:1867–1875.

Non-Viral Vectors

If viral vectors are not wanted, liposomal preparations can alternatively be used to deliver the nucleic acid molecules of the invention. Useful liposomal preparations include cationic (positively charged), anionic (negatively charged) and neutral preparations, with cationic liposomes particularly preferred. Cationic liposomes have been shown to mediate intracellular delivery of plasmid DNA (Felgner et al. (1987) *Proc. Natl. Acad. Sci. USA* 84:7413–7416) and mRNA (Malone et al. (1989) *Proc. Natl. Acad. Sci. USA* 86:6077–6081).

As yet another alternative to viral vector systems, the nucleic acid molecules of the present invention may be encapsulated, adsorbed to, or associated with, particulate carriers. Suitable particulate carriers include those derived from polymethyl methacrylate polymers, as well as PLG microparticles derived from poly(lactides) and poly(lactide-co-glycolides). See, e.g., Jeffery et al. (1993) *Pharm. Res.* 10:362–368. Other particulate systems and polymers can also be used, for example, polymers such as polylysine, polyarginine, polyornithine, spermine, spermidine, as well as conjugates of these molecules.

Particles

In one embodiment, the polynucleotides (e.g., DNA vaccines) and/or adjuvants are delivered using carrier particles. Particle-mediated methods for delivering such nucleic acid preparations are known in the art. Thus, once prepared and suitably purified, the above-described nucleic acid molecules and/or adjuvants can be coated onto carrier particles (e.g., core carriers) using a variety of techniques known in the art. Carrier particles are selected from materials which have a suitable density in the range of particle sizes typically used for intracellular delivery from a particle-mediated delivery device. The optimum carrier particle size will, of course, depend on the diameter of the target cells. Alternatively, colloidal gold particles can be used wherein the coated colloidal gold is administered (e.g., injected) into tissue (e.g., skin or muscle) and subsequently taken-up by immune-competent cells.

For the purposes of the invention, tungsten, gold, platinum and iridium carrier particles can be used. Tungsten and gold particles are preferred. Tungsten particles are readily available in average sizes of 0.5 to 2.0 µm in diameter. Although such particles have optimal density for use in particle acceleration delivery methods, and allow highly efficient coating with DNA, tungsten may potentially be toxic to certain cell types. Gold particles or microcrystalline gold (e.g., gold powder A1570, available from Engelhard Corp., East Newark, N.J.) will also find use with the present methods. Gold particles provide uniformity in size (available from Alpha Chemicals in particle sizes of 1–3 µm, or available from Degussa, South Plainfield, N.J. in a range of particle sizes including 0.95 µm) and reduced toxicity. Microcrystalline gold provides a diverse particle size distribution, typically in the range of 0.5–5 µm. However, the irregular surface area of microcrystalline gold provides for highly efficient coating with nucleic acids.

A number of methods are known and have been described for coating or precipitating DNA or RNA onto gold or tungsten particles. Most such methods generally combine a predetermined amount of gold or tungsten with plasmid DNA, $CaCl_2$ and spermidine. The resulting solution is vortexed continually during the coating procedure to ensure uniformity of the reaction mixture. After precipitation of the nucleic acid, the coated particles can be transferred to suitable membranes and allowed to dry prior to use, coated onto surfaces of a sample module or cassette, or loaded into a delivery cassette for use in particular particle-mediated delivery instruments.

Peptides (e.g., BCG), can also be coated onto suitable carrier particles, e.g., gold or tungsten. For example, peptides can be attached to the carrier particle by simply mixing the two components in an empirically determined ratio, by ammonium sulfate precipitation or solvent precipitation methods familiar to those skilled in the art, or by chemical coupling of the peptide to the carrier particle. The coupling of L-cysteine residues to gold has been previously described (Brown et al., *Chemical Society Reviews* 9:271–311 (1980)). Other methods include, for example, dissolving the peptide antigen in absolute ethanol, water, or an alcohol/water mixture, adding the solution to a quantity of carrier particles, and then drying the mixture under a stream of air or nitrogen gas while vortexing. Alternatively, the peptide antigens can be dried onto carrier particles by centrifugation under vacuum. Once dried, the coated particles can be resuspended in a suitable solvent (e.g., ethyl acetate or acetone), and triturated (e.g., by sonication) to provide a substantially uniform suspension.

Administration of Coated Particles

Following their formation, carrier particles coated with either nucleic acid preparations, or peptide or protein preparations, can be delivered to a subject, using particle-mediated delivery techniques.

Various particle acceleration devices suitable for particle-mediated delivery are known in the art, and are all suited for use in the practice of the invention. Current device designs employ an explosive, electric or gaseous discharge to propel coated carrier particles toward target cells. The coated carrier particles can themselves be releasably attached to a movable carrier sheet, or removably attached to a surface along which a gas stream passes, lifting the particles from the surface and accelerating them toward the target. An example of a gaseous discharge device is described in U.S. Pat. No. 5,204,253. An explosive-type device is described in U.S. Pat. No. 4,945,050. One example of an electric discharge-type particle acceleration apparatus is described in U.S. Pat. No. 5,120,657. Another electric discharge apparatus suitable for use herein is described in U.S. Pat. No. 5,149,655. The disclosure of all of these patents is incorporated herein by reference in their entireties.

The coated particles are administered to the subject to be treated in a manner compatible with the dosage formulation, and in an amount that will be effective to bring about a desired immune response. The amount of the composition to be delivered which, in the case of nucleic acid molecules is generally in the range of from 0.001 to 10.0 µg, more preferably 0.01 to 10.0 µg of nucleic acid molecule per dose, and in the case of peptide or protein molecules is 1 µg to 1 mg, more preferably 1 to 50 µg of peptide, depends on the subject to be treated. The exact amount necessary will vary depending on the age and general condition of the individual being immunized and the particular nucleotide sequence or peptide selected, as well as other factors. An appropriate effective amount can be readily determined by one of skill in the art upon reading the instant specification.

Thus, an effective amount of the antigens herein described, or nucleic acids coding therefor, will be sufficient to bring about a suitable immune response in an immunized subject, and will fall in a relatively broad range that can be determined through routine trials. Preferably, the coated particles are delivered to suitable recipient cells in order to bring about an immune response (e.g., T-cell activation) in the treated subject.

Particulate Compositions

Alternatively, the antigen of interest (as well as one or more selected adjuvant) can also be formulated as a particulate composition. More particularly, formulation of particles comprising the antigen and/or adjuvant of interest can be carried out using standard pharmaceutical formulation chemistries and methodologies all of which are readily available to the reasonably skilled artisan. For example, one or more antigens and/or adjuvants can be combined with one or more pharmaceutically acceptable excipient or vehicles to provide an antigen, adjuvant, or vaccine composition. Auxiliary substances, such as wetting or emulsifying agents, pH buffering substances, and the like, may be present in the excipient or vehicle. These excipients, vehicles and auxiliary substances are generally pharmaceutical agents that do not themselves induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. It is also preferred, although not required, that an antigen composition will contain a pharmaceutically acceptable excipient that serves as a stabilizer, particularly for peptide, protein or other like antigens. Examples of suitable carriers that also act as stabilizers for peptides include, without limitation, pharmaceutical grades of dextrose, sucrose, lactose, trehalose, mannitol, sorbitol, inositol, dextran, and the like. Other suitable carriers include, again without limitation, starch, cellulose, sodium or calcium phosphates, citric acid, tartaric acid, glycine, high molecular weight polyethylene glycols (PEGs), and combination thereof. A thorough discussion of pharmaceutically acceptable excipients, carriers, stabilizers and other auxiliary substances is available in REMINGTON'S PHARMACEUTICAL SCIENCES (Mack Pub. Co., N.J. 1991), incorporated herein by reference.

The formulated compositions will include an amount of the antigen of interest which is sufficient to mount an immunological response, as defined above. An appropriate effective amount can be readily determined by one of skill in the art. Such an amount will fall in a relatively broad range, generally within the range of about 0.1 µg to 25 mg or more of the antigen of interest, and specific suitable amounts can be determined through routine trials. The compositions may contain from about 0.1% to about 99.9% of the antigen. If an adjuvant is included in the composition, or the methods are used to provide a particulate adjuvant composition, the adjuvant will be present in a suitable amount as described above. The compositions are then prepared as particles using standard techniques, such as by simple evaporation (air drying), vacuum drying, spray drying, freeze drying (lyophilization), spray-freeze drying, spray coating, precipitation, supercritical fluid particle formation, and the like. If desired, the resultant particles can be densified using the techniques described in commonly owned International Publication No. WO 97/48485, incorporated herein by reference.

These methods can be used to obtain nucleic acid particles having a size ranging from about 0.1 to about 250 µm, preferably about 10 to about 150 µm, and most preferably about 20 to about 60 µm; and a particle density ranging from about 0.1 to about 25 g/cm$^3$, and a bulk density of about 0.5 to about 3.0 g/cm$^3$, or greater.

Similarly, particles of selected adjuvants having a size ranging from about 0.1 to about 250 µm, preferably about 0.1 to about 150 µm, and most preferably about 20 to about 60 µm; a particle density ranging from about 0.1 to about 25 g/cm$^3$, and a bulk density of preferably about 0.5 to about 3.0 g/cm$^3$, and most preferably about 0.8 to about 1.5 g/cm$^3$ can be obtained.

Single unit dosages or multidose containers, in which the particles may be packaged prior to use, can comprise a hermetically sealed container enclosing a suitable amount of the particles comprising the antigen of interest and/or the selected adjuvant (e.g., the vaccine composition). The particulate compositions can be packaged as a sterile formulation, and the hermetically sealed container can thus be designed to preserve sterility of the formulation until use in the methods of the invention. If desired, the containers can be adapted for direct use in a needleless syringe system. Such containers can take the form of capsules, foil pouches, sachets, cassettes, and the like. Appropriate needleless syringes are described herein above.

The container in which the particles are packaged can further be labeled to identify the composition and provide relevant dosage information. In addition, the container can be labeled with a notice in the form prescribed by a governmental agency, for example the Food and Drug Administration, wherein the notice indicates approval by the agency under Federal law of the manufacture, use or sale of the antigen, adjuvant (or vaccine composition) contained therein for human administration.

Administration of Particulate Compositions

Following their formation, the particulate composition (e.g., powder) can be delivered transdermally to the subject's tissue using a suitable transdermal delivery technique. Various particle acceleration devices suitable for transdermal delivery of the substance of interest are known in the art, and will find use in the practice of the invention. A particularly preferred transdermal delivery system employs a needleless syringe to fire solid drug-containing particles in controlled doses into and through intact skin and tissue. See, e.g., U.S. Pat. No. 5,630,796 to Bellhouse et al. which describes a needleless syringe (also known as "the PowderJect® needleless syringe device"). Other needleless syringe configurations are known in the art and are described herein.

The particulate compositions (comprising the antigen of interest and/or a selected adjuvant) can be administered using a transdermal delivery technique. Preferably, the particulate compositions will be delivered via a powder injection method, e.g., delivered from a needleless syringe system such as those described in commonly owned International Publication Nos. WO 94/24263, WO 96/04947, WO 96/12513, and WO 96/20022, all of which are incorporated herein by reference. Delivery of particles from such needleless syringe systems is typically practised with particles having an approximate size generally ranging from 0.1 to 250 µm, preferably ranging from about 10–70 µm. Particles larger than about 250 µm can also be delivered from the devices, with the upper limitation being the point at which the size of the particles would cause untoward damage to the skin cells. The actual distance which the delivered particles will penetrate a target surface depends upon particle size (e.g., the nominal particle diameter assuming a roughly spherical particle geometry), particle density, the initial velocity at which the particle impacts the surface, and the density and kinematic viscosity of the targeted skin tissue. In this regard, optimal particle densities for use in needleless injection generally range between about 0.1 and 25 g/cm$^3$, preferably between about 0.9 and 1.5 g/cm$^3$, and injection velocities generally range between about 100 and 3,000 m/sec, or greater. With appropriate gas pressure, particles having an average diameter of 10–70 µm can be accelerated through the nozzle at velocities approaching the supersonic speeds of a driving gas flow.

If desired, these needleless syringe systems can be provided in a preloaded condition containing a suitable dosage of the particles comprising the antigen of interest and/or the selected adjuvant. The loaded syringe can be packaged in a hermetically sealed container, which may further be labeled as described above.

Compositions containing a therapeutically effective amount of the powdered molecules described herein can be delivered to any suitable target tissue via the above-described needleless syringes. For example, the compositions can be delivered to muscle, skin, brain, lung, liver, spleen, bone marrow, thymus, heart, lymph, blood, bone cartilage, pancreas, kidney, gall bladder, stomach, intestine, testis, ovary, uterus, rectum, nervous system, eye, gland and connective tissues. For nucleic acid molecules, delivery is preferably to, and the molecules expressed in, terminally differentiated cells; however, the molecules can also be delivered to non-differentiated, or partially differentiated cells such as stem cells of blood and skin fibroblasts.

The powdered compositions are administered to the subject to be treated in a manner compatible with the dosage formulation, and in an amount that will be prophylactically and/or therapeutically effective. The amount of the composition to be delivered, generally in the range of from 0.5 µg/kg to 100 µg/kg of nucleic acid molecule per dose, depends on the subject to be treated. Doses for other pharmaceuticals, such as physiological active peptides and proteins, generally range from about 0.1 µg to about 20 mg, preferably 10 µg to about 3 mg. The exact amount necessary will vary depending on the age and general condition of the individual to be treated, the severity of the condition being treated, the particular preparation delivered, the site of administration, as well as other factors. An appropriate effective amount can be readily determined by one of skill in the art.

Thus, a "therapeutically effective amount" of the present particulate compositions will be sufficient to bring about treatment or prevention of disease or condition symptoms, and will fall in a relatively broad range that can be determined through routine trials.

Pharmaceutical Compositions

Formulation of a composition comprising the above recombinant nucleic acid molecules can be carried out using standard pharmaceutical formulation chemistries and methodologies all of which are readily available to the reasonably skilled artisan. For example, compositions containing one or more nucleic acid molecules can be combined with one or more pharmaceutically acceptable excipients or vehicles. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Certain facilitators of nucleic acid uptake and/or expression can also be included in the compositions, for example, facilitators such as bupivacaine, cardiotoxin and sucrose. A thorough discussion of pharmaceutically acceptable excipients, vehicles and auxiliary substances is available in REMINGTON'S PHARMACEUTICAL SCIENCES (Mack Pub. Co., N.J. 1991), incorporated herein by reference.

The formulated compositions will include an amount of the *M. tuberculosis* antigens of interest sufficient to mount an immunological response, as defined above. An appropriate effective amount can be readily determined by one of skill in the art. Such an amount will fall in a relatively broad range that can be determined through routine trials. The compositions may contain from about 0.1% to about 99.9% of the antigens and can be administered directly to the subject or, alternatively, delivered ex vivo, to cells derived from the subject, using methods known to those skilled in the art. For example, methods for the ex vivo delivery and reimplantation of transformed cells into a subject are known (e.g., dextran-mediated transfection, calcium phosphate precipitation, electroporation, and direct microinjection of into nuclei). Methods for in vivo delivery can entail injection using a conventional syringe. The constructs can be injected either subcutaneously, epidermally, intradermally, intramucosally such as nasally, rectally and vaginally, intraperitoneally, intravenously, orally or intramuscularly. Other modes of administration include oral and pulmonary administration, suppositories, and transdermal applications.

Furthermore, it is also intended that the polynucleotides delivered by the methods of the present invention be combined with other suitable compositions and therapies. For instance, in order to augment an immune response in a subject, the compositions and methods described herein can further include ancillary substances (e.g., adjuvants), such as pharmacological agents, cytokines, or the like. Suitable adjuvants include any substance that enhances the immune response of the subject to the antigen-encoding polynucleotide fragments of the invention. Ancillary substances may be administered, for example, as proteins or other macromolecules at the same time, prior to, or subsequent to, administration of the DNA vaccines described herein.

Eliciting Immune Responses

In another embodiment of the invention, a method for eliciting an anti-*M. tuberculosis* immune response in a subject is provided. In one aspect, the method entails transfected cells of the subject (in vivo or ex vivo) with a nucleic acid composition that includes one or more polynucleotides encoding one or more *M. tuberculosis* antigens in an amount sufficient to induce an immune response. Preferably, the polynucleotides are delivered by coating core carriers (e.g., via particle-mediated delivery techniques) or transdermally (e.g., via needless syringe technology). In particular, as more fully described below in the Examples, delivery of these polynucleotides using particle-mediated delivery techniques shows a greater than 1-log fold (10 fold) reduction in spleen bacteria counts when compared to intramuscular polynucleotide immunization (see, e.g., accompanying FIG. 11B as compared to FIGS. 16–20 of U.S. Pat. No. 5,736,524).

In another aspect, the method entails transfecting cells of the subject with a nucleic acid composition that includes one or more recombinant nucleic acid molecules having a sequence or sequences encoding a plurality of *M. tuberculosis* antigens (as described herein above) in a priming step, and then administering a secondary composition to the subject in one or more boosting steps, wherein the secondary composition comprises, or encodes the same or different antigens as in the nucleic acid composition. Thus, the secondary composition can be any suitable vaccine composition which contains one or more nucleic acid molecules encoding the *M. tuberculosis* antigens interest, or a composition containing the *M. tuberculosis* antigens of interest in peptide or protein form. In one preferred embodiment, the secondary composition comprises BCG. The present inventors have determined that using the polynucleotides described herein as the priming immunization and BCG as a booster provides substantially enhanced protection as compared to BCG alone, BCG prime with BCG boost and polynucleotides alone.

Direct delivery of the secondary compositions in vivo will generally be accomplished with or without viral vectors (e.g., a modified vaccinia vector) as described above, by injection using either a conventional syringe, or using a particle-mediated delivery system as also described above. Injection will typically be either subcutaneously, epidermally, intradermally, intramucosally (e.g., nasally, rectally and/or vaginally), intraperitoneally, intravenously, orally or intramuscularly. Other modes of administration include oral and pulmonary administration, suppositories, and transdermal applications. Dosage treatment may be a single dose schedule or a multiple dose schedule.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Figure 2:
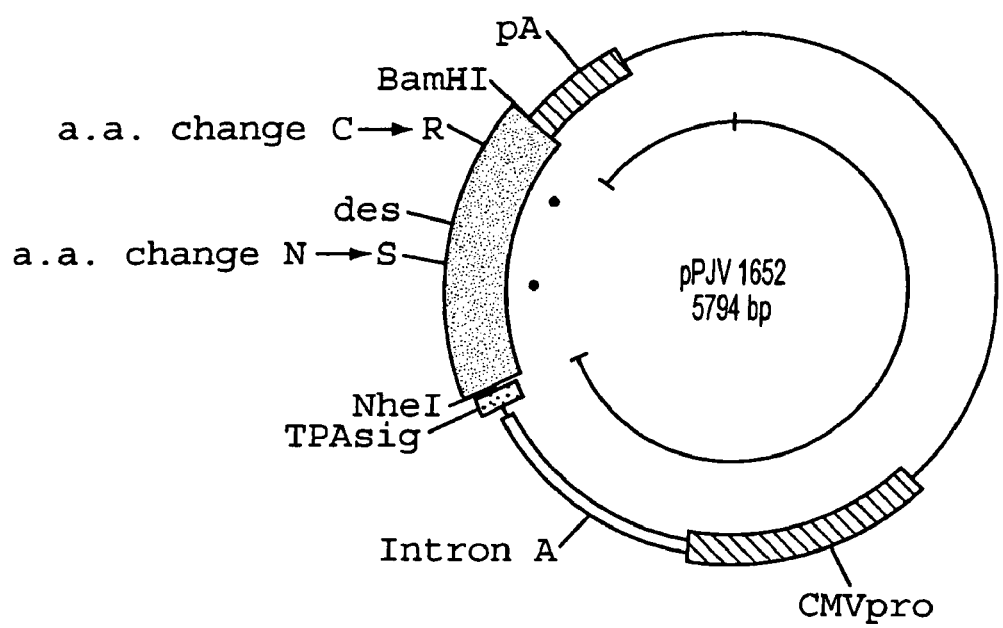
Figure 3:
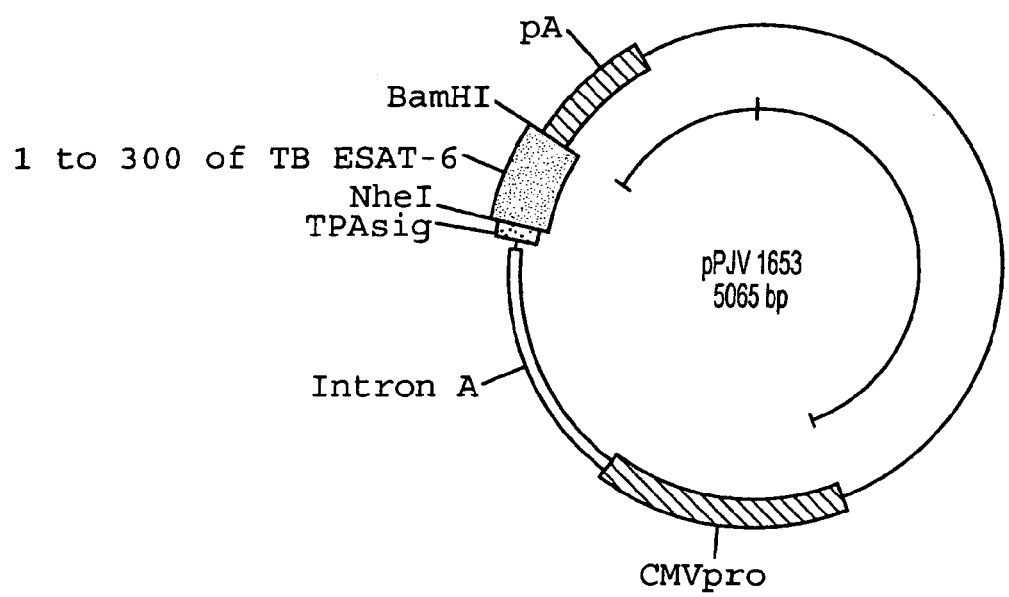
Figure 4:
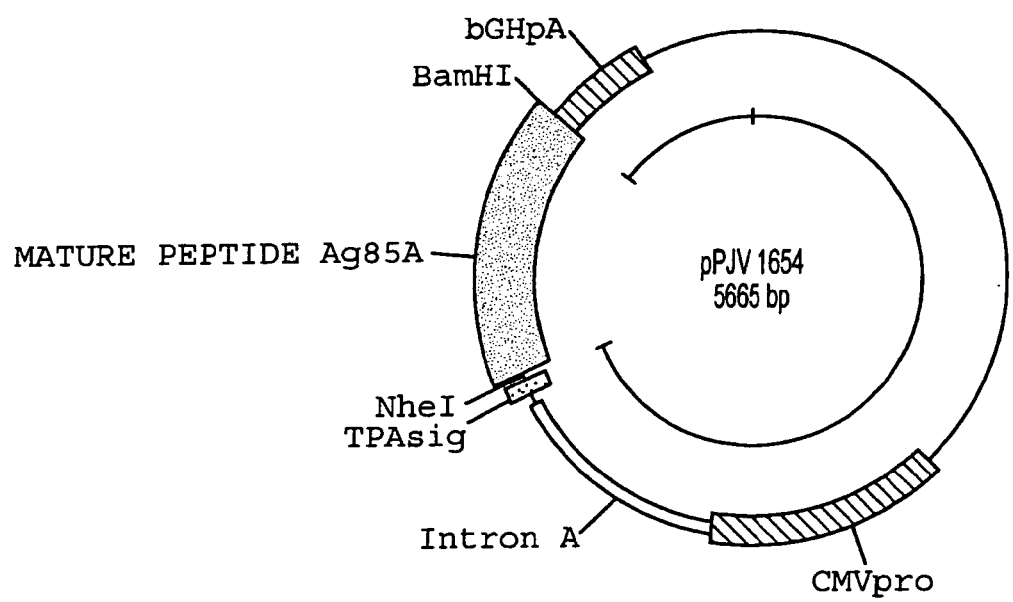
Figure 5:
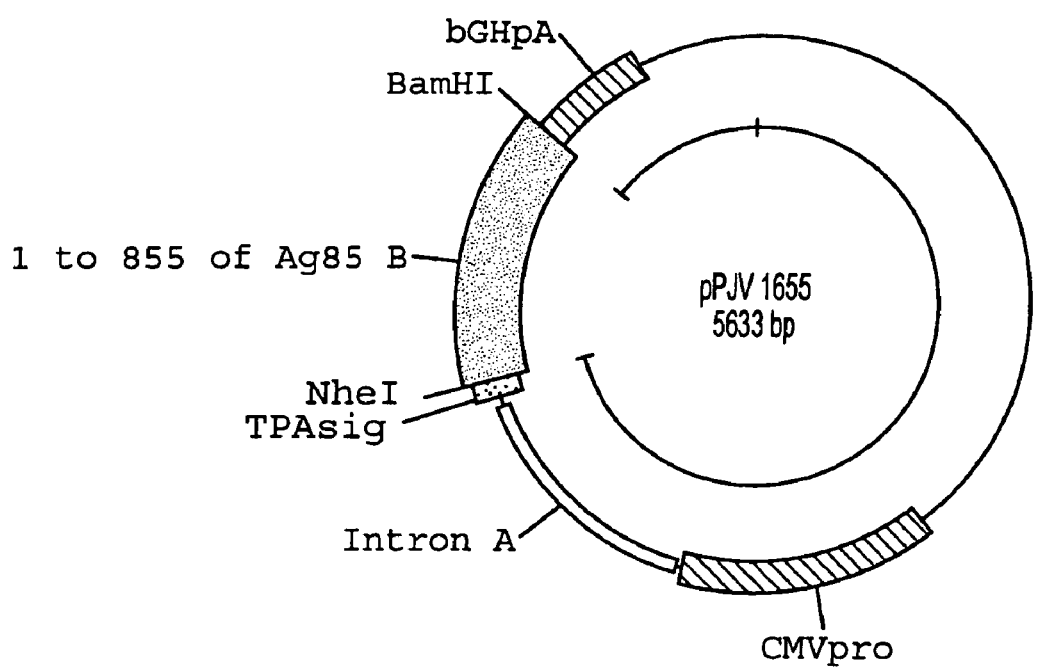
Figure 6:
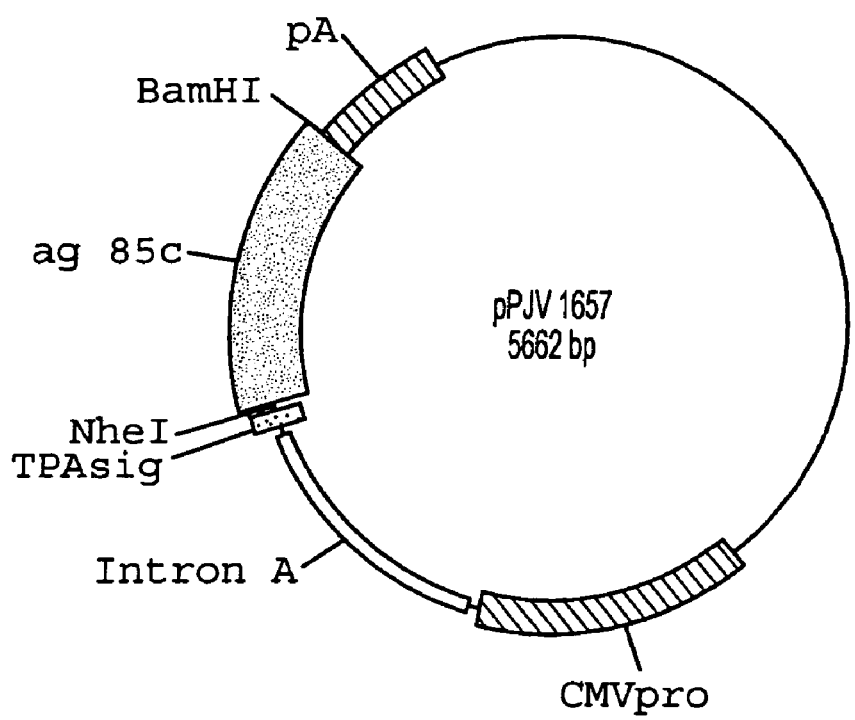
Figure 7:
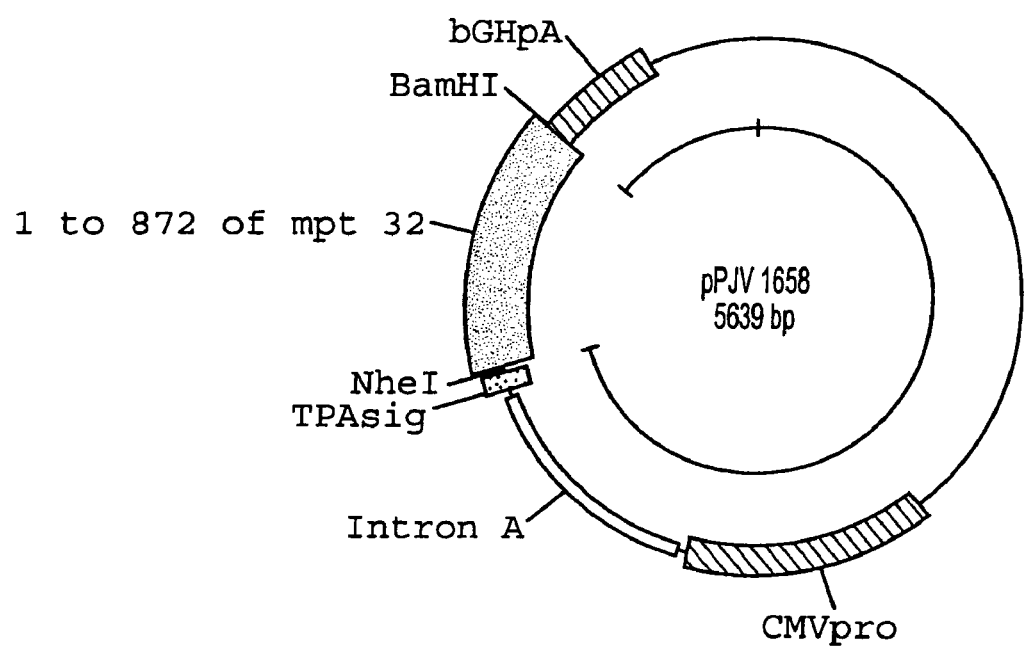
Figure 8:
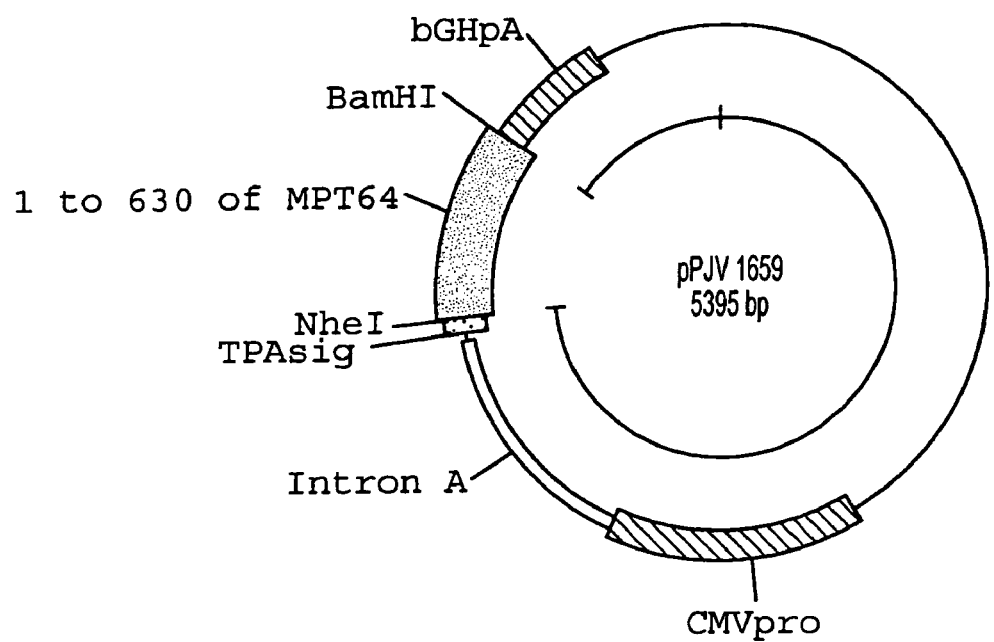
Figure 9:
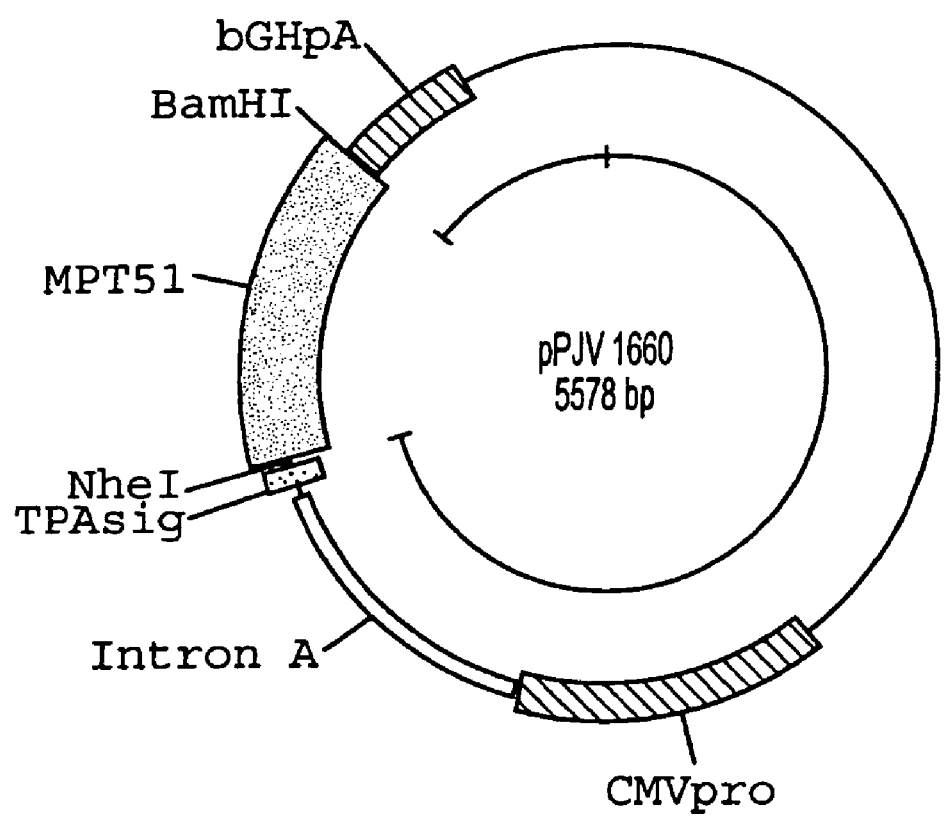
Figure 10:
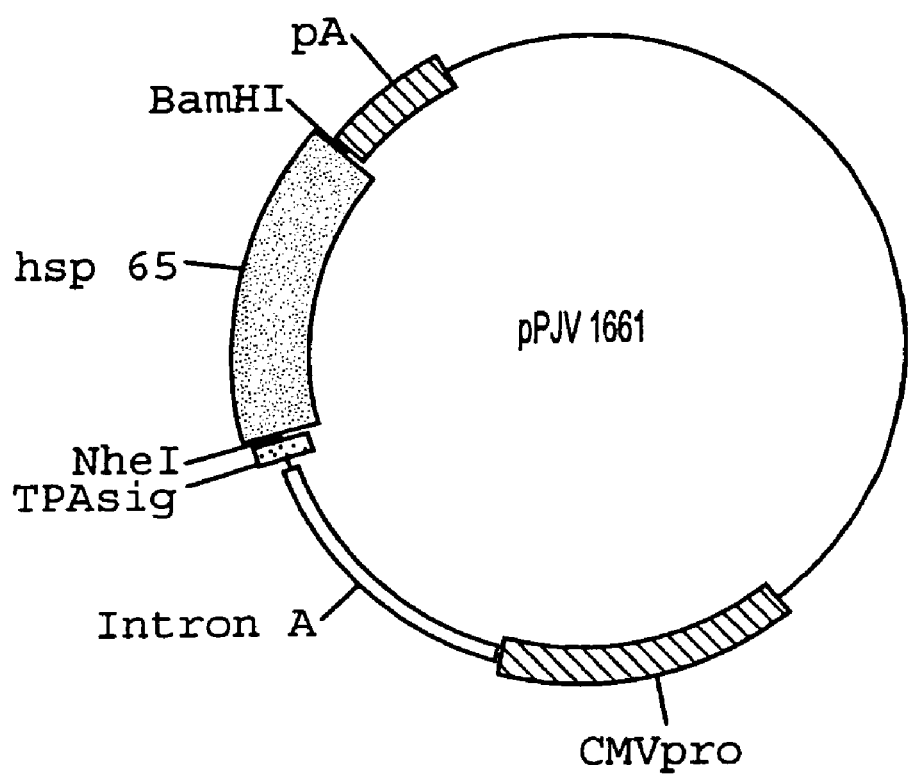

Example 1: Plasmid Construction
The expression plasmids used for the M tuberculosis DNA vaccine are listed in the following table:

| Plasmid Name | Encoded M. tuberculosis Gene |
|---|---|
| pPJV1651 (FIG. 1) | MPT 63 |
| pPJV1652 (FIG. 2) | DES |
| pPJV1653 (FIG. 3) | ESAT-6 |
| pPJV1654 (FIG. 4) | 85A |
| pPJV1655 (FIG. 5) | 85B |
| pPJV1657 (FIG. 6) | 85C |
| pPJV1658 (FIG. 7) | M13T32 |
| pPJV1659 (FIG. 8) | MPT64 |
| pPJV1660 (FIG. 9) | MPT 51 |
| pPJV1661 (FIG. 10) | hsp65 |

The plasmids pPJV1651–pPJV1661 were cloned from *M. tuberculosis* H37Rv genomic DNA using PCR technology. The oligonucleotides used to amplify the *M. tuberculosis* genes are listed below:

```
Oligos for amplifying TB genes for cocktail DNA vaccine

Antigen 85A forward primer
5' GGA GCT AGC GCA TTT TCC CGG CCG GGC TTG 3' (SEQ ID NO:1)

Antigen 85A reverse primer
5' GGT GGA TCC CTA GGC GCC CTG GGG CGC 3' (SEQ ID NO:2)

Antigen 85B forward primer
5' GGA GCT AGC TTC TCC CGG CCG GGG CTG 3' (SEQ ID NO:3)

Antigen 85B reverse primer
5' GGT GGA TCC TCA GCC GGC GCC TAA CGA 3' (SEQ ID NO:4)

Antigen 85C forward primer
5' GGA GCT AGC TTC TCT AGG CCC GGT CTT 3' (SEQ ID NO:5)

Antigen 85C reverse primer
5' GGT GGA TCC TCA GGC GGC CGG CGC AGC 3' (SEQ ID NO:6)

ESAT-6 forward primer
5' GGA GCT AGC ATG ACA GAG CAG CAG TGG AAT 3' (SEQ ID NO:7)

ESAT-6 reverse primer
5' GGT GGA TCC CTA TGC GAA CAT CCC AGT GAC 3' (SEQ ID NO:8)

DES forward primer
5' GGA GCT AGC ATG TCA GCC AAG CTG ACC GA 3' (SEQ ID NO:9)

DES reverse primer
5' GGT GGA TCC CTA ACG ACG GCT CAT CGC CAG 3' (SEQ ID NO:10)

MPT 51 forward primer
5' GGA GCT AGC GCC CCA TAC GAG AAC CTG ATG 3' (SEQ ID NO:11)
```

-continued

```
MPT 51 reverse primer
5' CCT GGA TCC TTA GCG GAT CGC ACC GAC GAT 3'  (SEQ ID NO:12)

MPT 32 (45/47 gene) forward primer
5' GGA GCT AGC GAT CCG GAG CCA GCG CCC CCG 3'  (SEQ ID NO:13)

MPT 32 (45/47 gene) reverse primer
5' CCT GGA TCC TCA GGC CGG TAA GGT CCG CTG 3'  (SEQ ID NO:14)

MPT 64 forward primer
5' GGA GCT AGC GCG CCC AAG ACC TAC TGC GAG 3'  (SEQ ID NO:15)

MPT 64 reverse primer
5' CCT GGA TCC CTA GGC CAG CAT CGA GTC GAT 3'  (SEQ ID NO:16)

MPT 63 forward primer
5' GGG CTA GCG CCT ATC CCA TCA CCG GAA AAC TTG GCA GTG A 3'  (SEQ ID NO:17)

MPT 63 reverse primer
5' GGA TCC CTA CGG CTC CCA AAT CAG CAG ATC CTC CAT 3'  (SEQ ID NO:18)

hsp65 forward primer
5' GGA GCT AGC ATG GCC AAG ACA ATT GCG TAC 3'  (SEQ ID NO:19)

hsp65 reverse primer
5' CCT GGA TCC TCA GAA ATC CAT GCC ACC CAT 3'  (SEQ ID NO:20)
```

PCR was conducted using the following conditions: a denaturing step at 95° C. for 2 minutes; an amplification step consisting of 30 cycles of 95° C. for 1 minute, 55° C. for 2 minutes and 15 seconds (annealing step) and 72° C. for 1 minute (extension step); a polishing step at 72° C. for 5 minutes and a holding step at 4° C. The PCR amplicons were cloned into pWRG7054. pWRG7054 is a pUC19 based vector that includes regulatory elements from pJW4303 (see, Chapman et al. (1991) *Nucleic Acids Res.* 19:3979–3986), in particular, the human cytomegalovirus immediate-early enhancer/promoter with intron A, the coding sequence for the tissue plasminogen activator (tPA) signal sequence, and the bovine growth hormone polyadenylation sequence. The PCR oligonucleotides were designed to clone the *M. tuberculosis* genes in frame with the tPA signal sequence.

Example 2

*M. tuberculosis* Vaccine/Challenge Study

Vaccine compositions comprising one or more of the nucleic acid molecules of the present invention were administered to guinea pig subjects in a vaccine/challenge study. The guinea pig model of *tuberculosis* is known and accepted in the art. In this regard, guinea pigs are susceptible to *tuberculosis* and, upon exposure, develop strong immunity against the *tuberculosis* causative agent which limits bacterial growth and damage to the lungs. This immune response is associated with considerable tissue damage, leading to extensive caseation and tissue necrosis that eventually kills the animal. As such, the guinea pig model is extremely useful in studies of events in infected humans which follow a similar pattern. Baldwin et al. (1998) *Infect. and Immun.* 66:2951–2959.

The nucleotide sequences for the following *M. tuberculosis* antigens were obtained and inserted into WRG7054 expression vectors using standard molecular biology techniques: Antigen 85A, Antigen 85B, Antigen 85C, ESAT-6, Des Protein, MPT32, MPT51, MPT63, MPT64, and HSP65. Various combinations of these ten resulting *M. tuberculosis* antigen recombinant WRG7054 plasmid constructs were used to form cocktail compositions for the vaccination study.

*M. tuberculosis* H37Rv and *M. bovis* BCG Pasteur cultures (Copenhagan 1331) were obtained from a commercial source, grown to early mid-log phase, and aliquots were stored at −70° C. until used.

Six cohorts consisting of ten guinea pigs were immunized three times at monthly intervals (days 0, 30 and 60) with various vaccines against *M. tuberculosis* as follows: Group A (DNA encoding 85A, the most immunogenic antigen of the ten candidate plasmids). Administration of 85A alone also allowed for direct comparison of immunization using particle-mediated delivery techniques to IM immunization (U.S. Pat. No. 5,736,524); Group B (DNA encoding 85A and MPT32, the two most immunogenic antigens of the ten plasmids); Group Ca (DNA encoding cocktail including 85A, 85B, 85C, MPT32, MPT51, MPT63, MPT64, Des, ESAT-6 and hsp65, to mimic immunization with culture filtrate proteins); Group Cb (priming with DNA cocktail vaccine composed of (85A, 85B, 85C, MPT32, MPT51, MPT63, MPT64, Des, ESAT-6 and hsp65) and boosting with BCG, to induce a synergistic immune response by immunization with a DNA vaccine prime followed by a (protein or attenuated virus or attenuated bacteria vaccine) boost and to compare protection elicited by BCG alone, which is the "Golden Standard" for *tuberculosis* vaccines); Group D (Negative Control, plasmid backbone-pUC19); Group E (Positive control, BCG). All DNA administrations were carried out using a PowderJect™ XR particle-mediated delivery device (PowderJect Vaccines, Madison, Wis.) with the appropriate plasmids loaded onto gold particles at 2.5 µg/mg Au. The gold particles were administered in four 0.5 mg Au shots for each dose (two shots on the left inguinal area and two shots on the right inguinal area for a total dose of 5 µg DNA) with the particle-mediated delivery device set at 500 psi. BCG was administered intradermally (i.d.) at about $10^3$ bacilli/guinea pig. The bacilli were administered in sterile saline and injected into the inguinal artery.

One month after the third immunization the guinea pigs were challenged with *M. tuberculosis* by aerogenic infection. Five weeks after challenge five guinea pigs from each group were sacrificed for histological analysis of the lungs and spleens and for the determination of the bacterial loads in the lungs and spleens. Histological assays and lung and spleen bacterial load determinations are then carried out to compare and contrast the protective efficacy of each vaccine strategy. Histology is carried out by fixing tissue in 10% neutral buffered formalin for routine microscopic processing. All tissues are stained with hematoxylin and eosin (H & E). For each animal, the left lower lobe is sagittally sectioned through the middle of the lobe. The following parameters are used to subjectively assess the tissue sections: severity (degree of parenchymal involvement), size of typical granulomas, amount of caseous necrosis, relative number of neutrophils and lymphocytes, degree to which lymphocytes are organized in the granuloma, and extent to which granulomas are organized. Bacterial load determinations are carried out by finely dividing lung and spleen tissue and then culturing the tissue in an appropriate growth medium. The five remaining animals of each group were retained for survival/weight loss studies.

Bacterial Loads in Lungs and Spleens

Figure 11A:
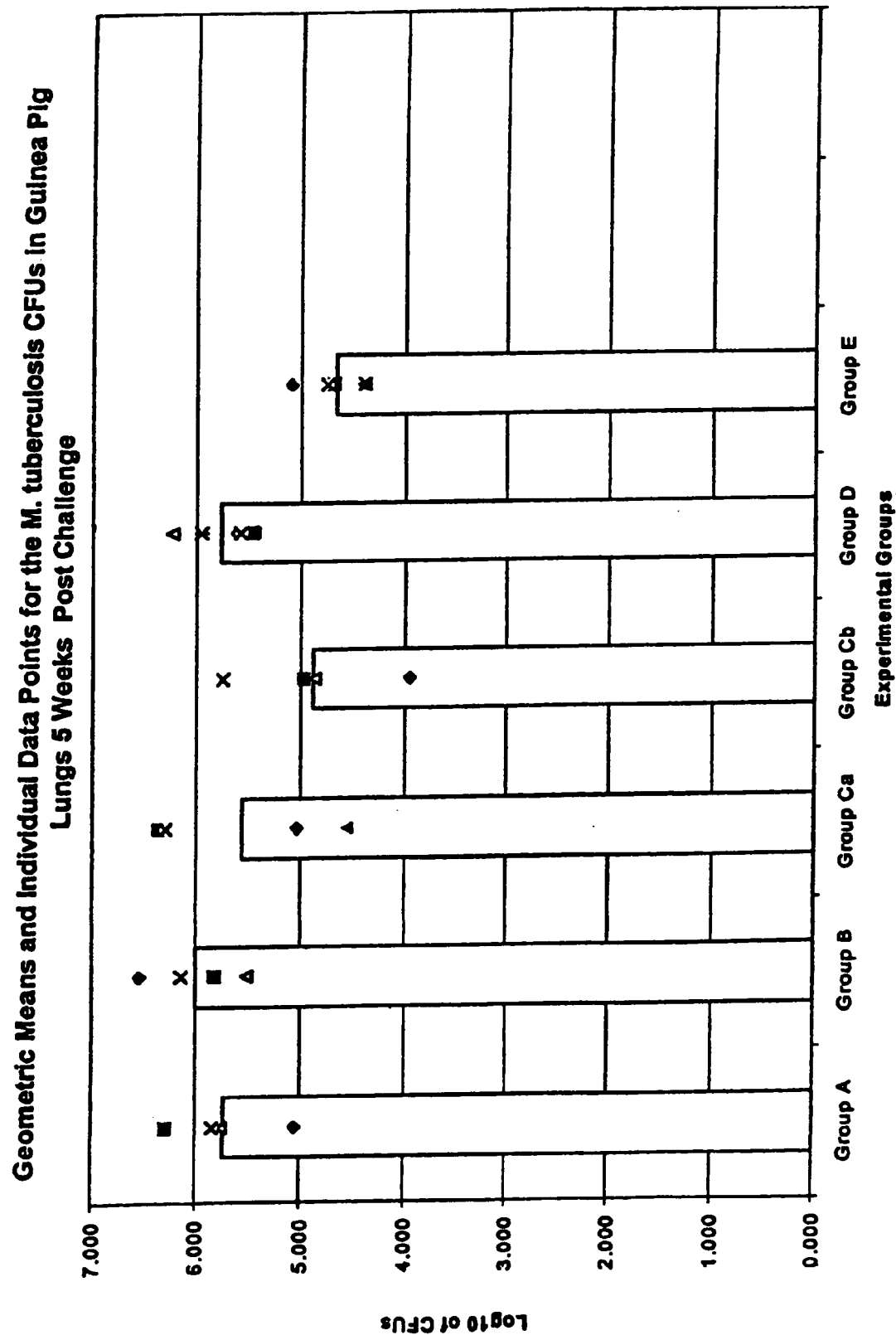
Figure 11B:
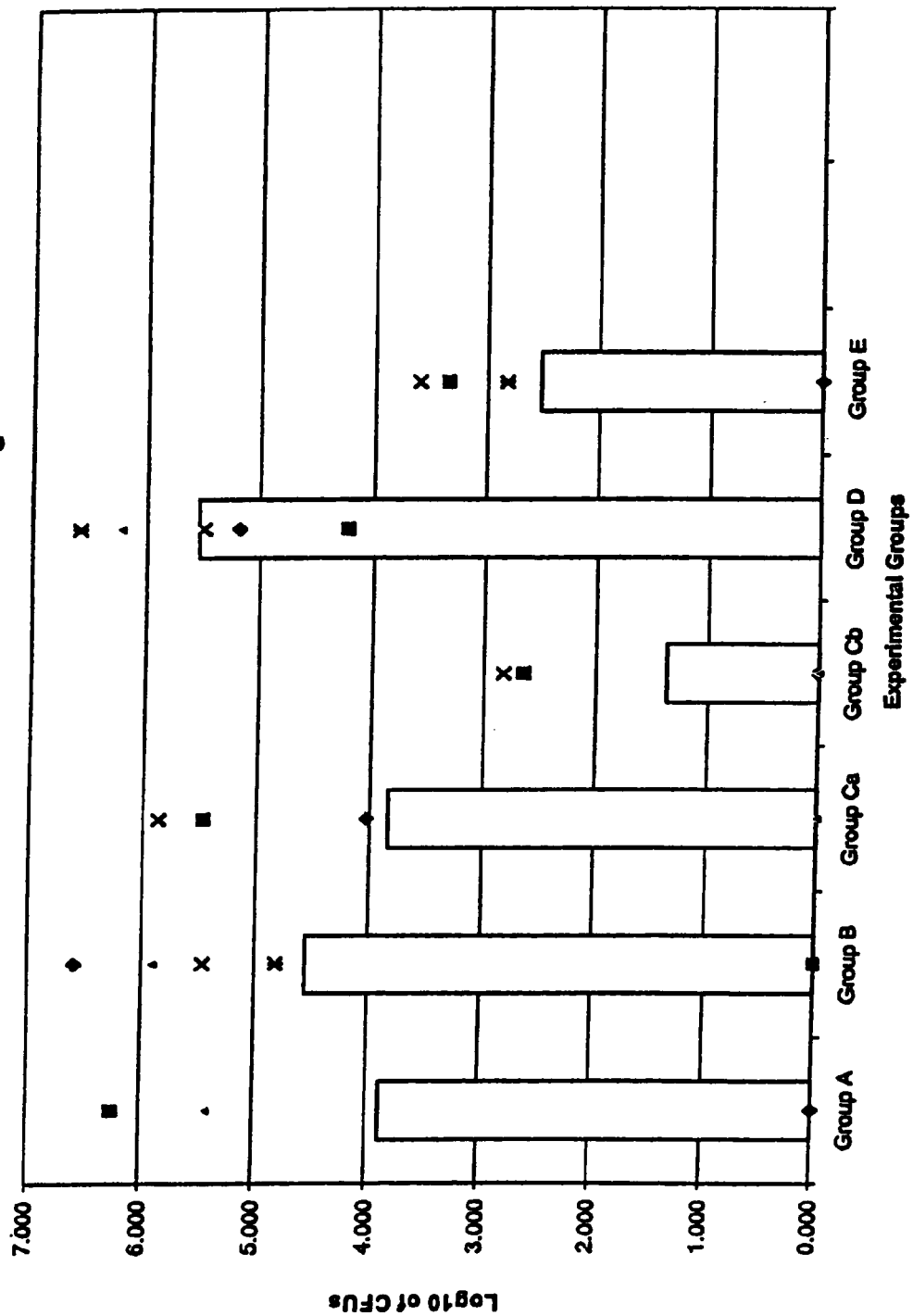
Figure 12A:
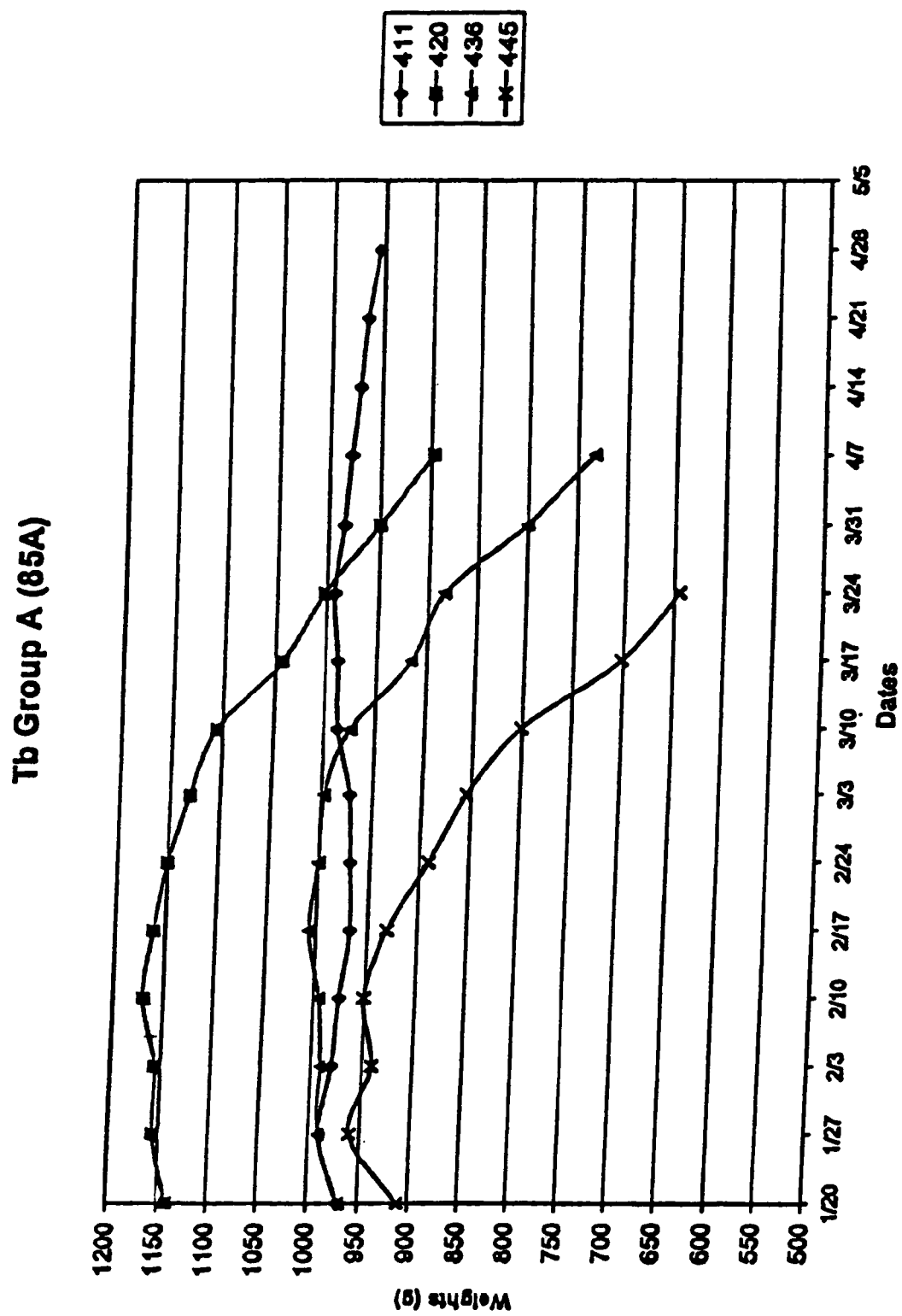
Figure 12B:
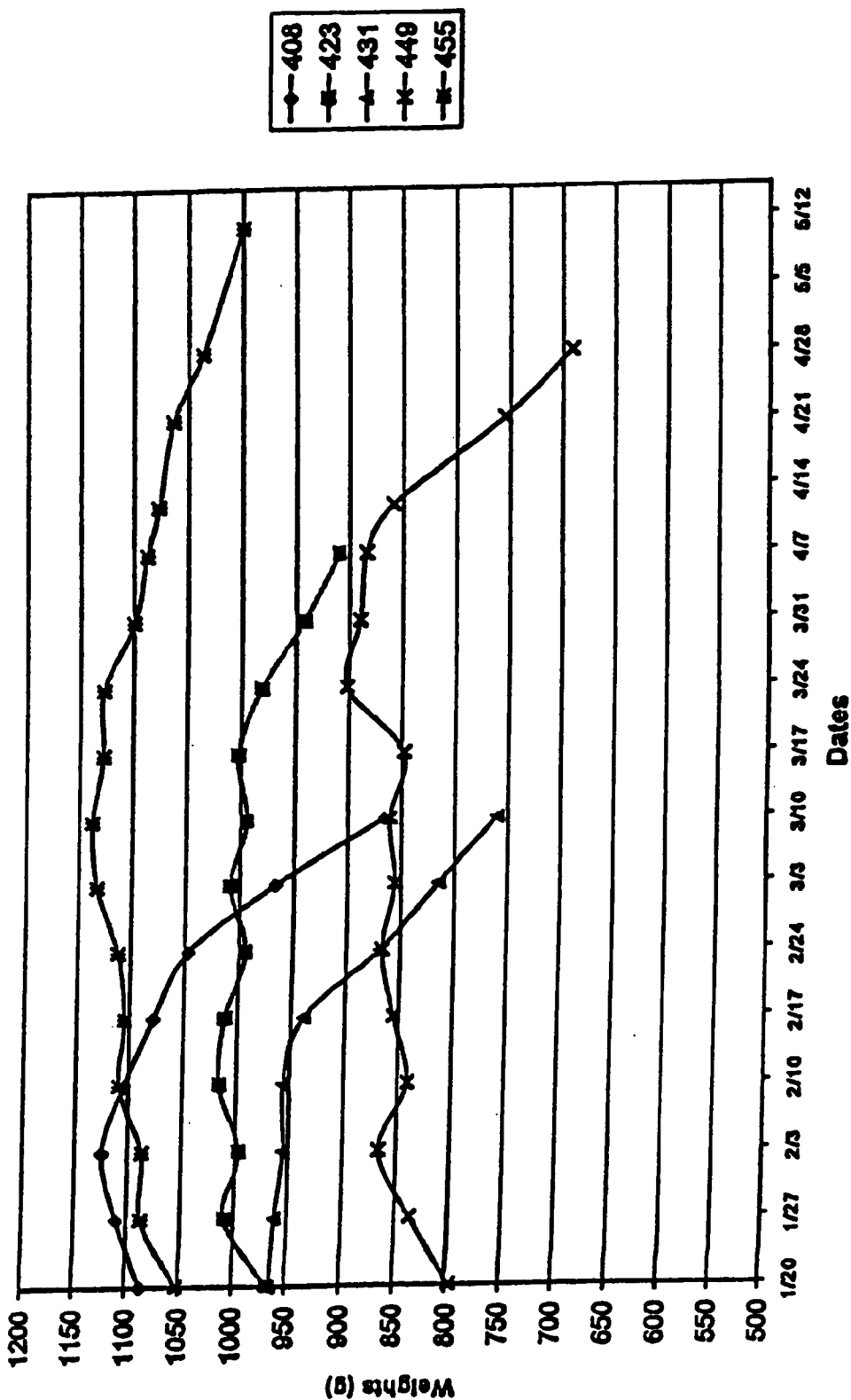
Figure 12C:
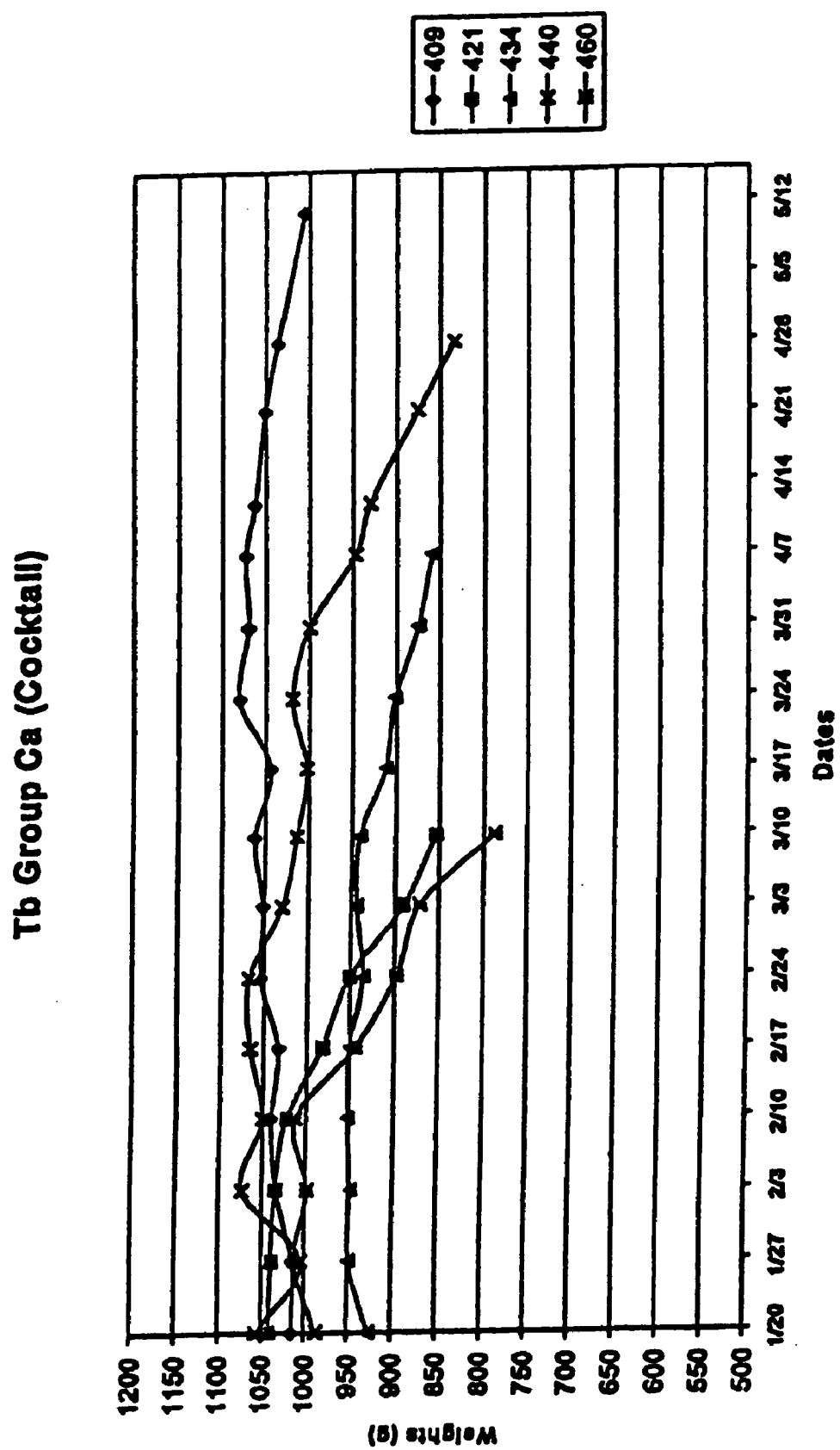
Figure 12D:
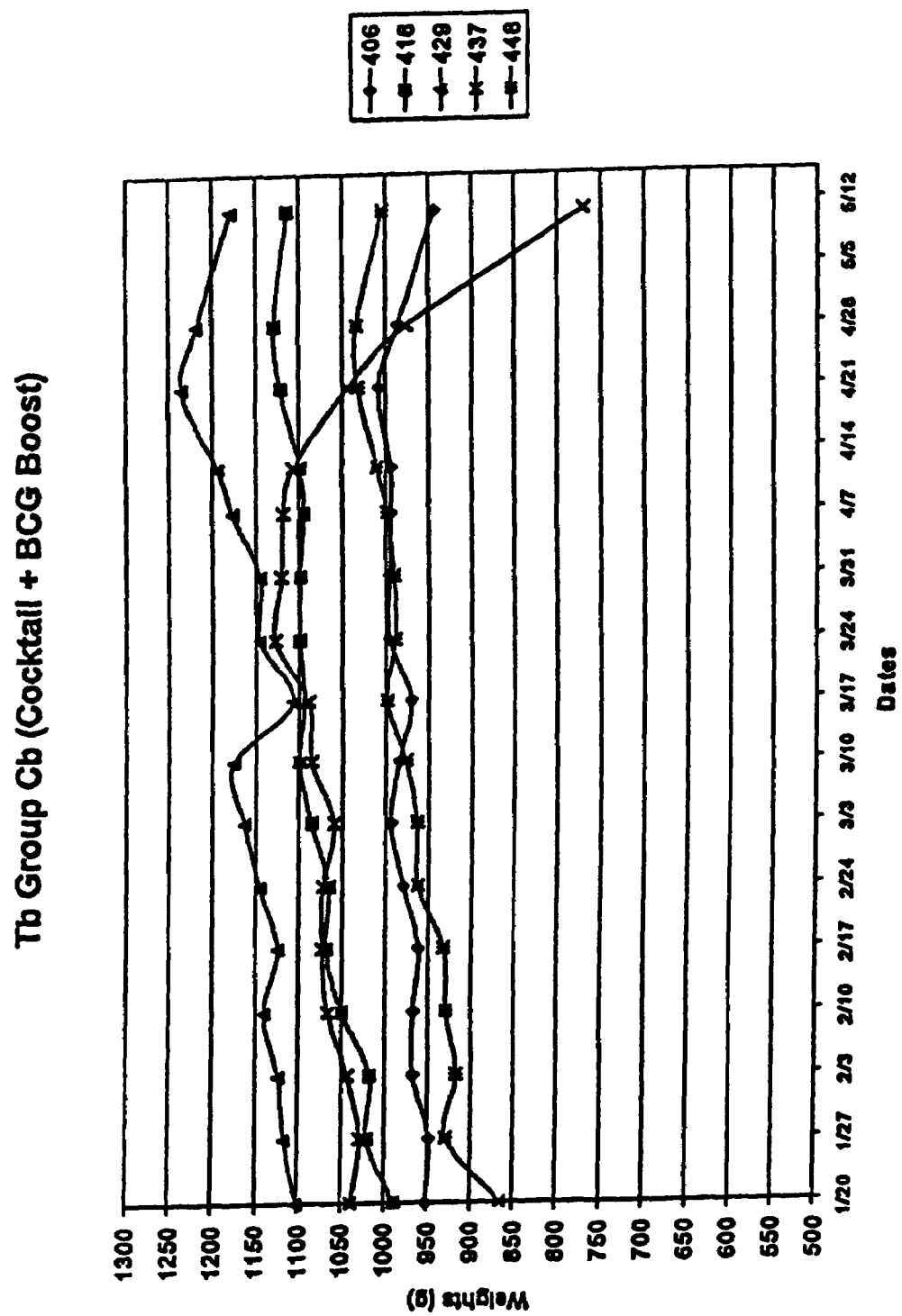
Figure 12E:
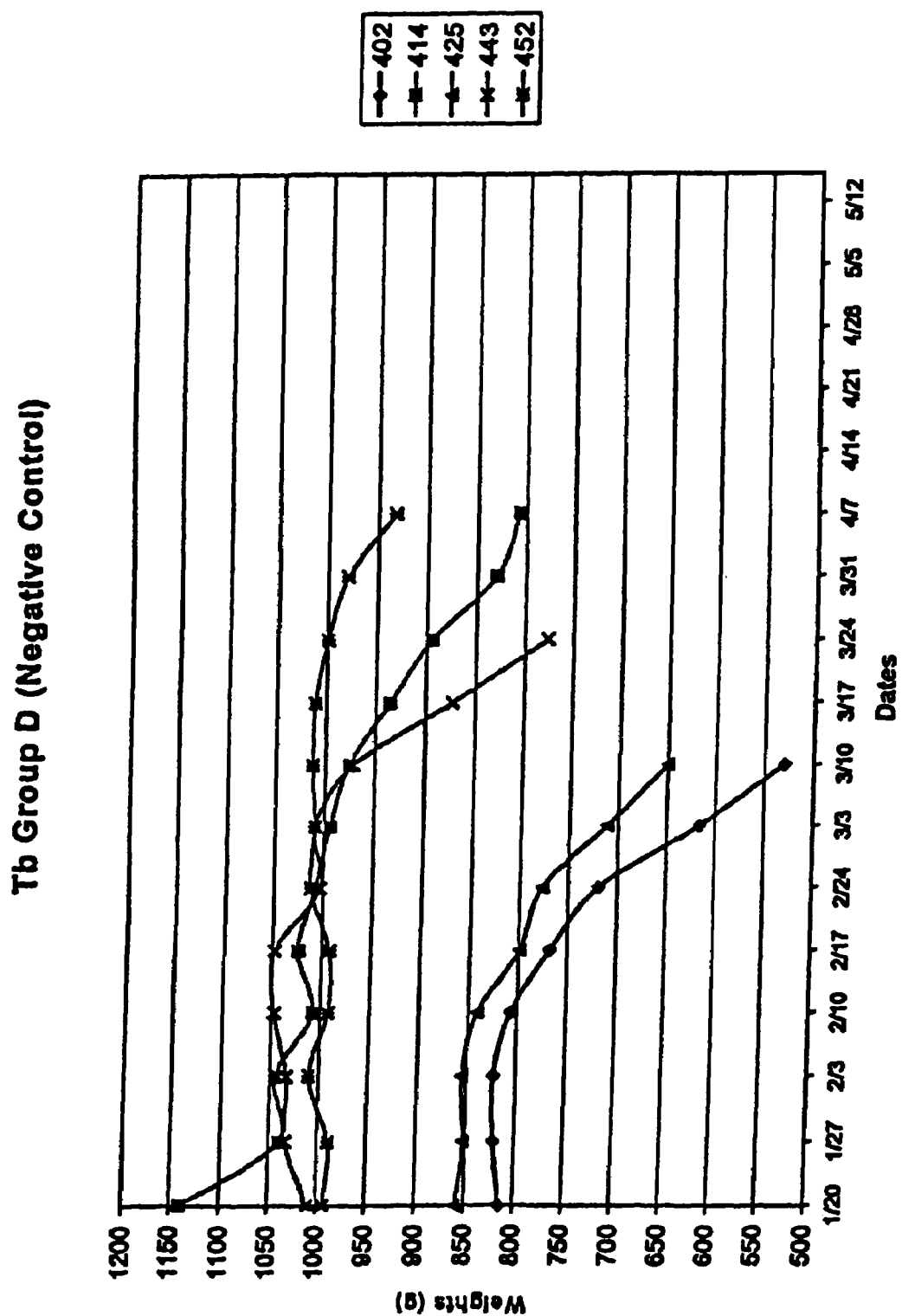
Figure 12F:
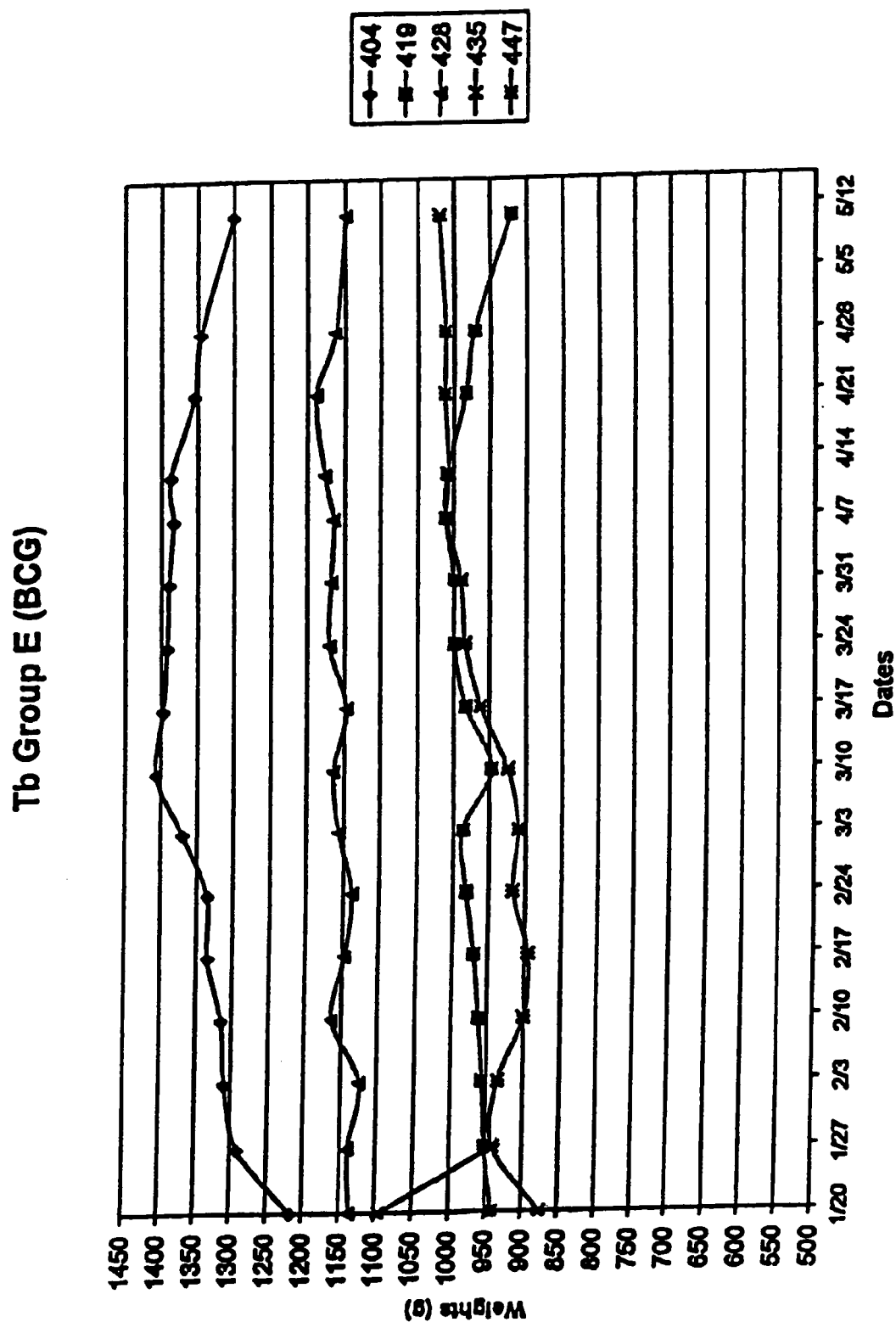
Figure 13A:
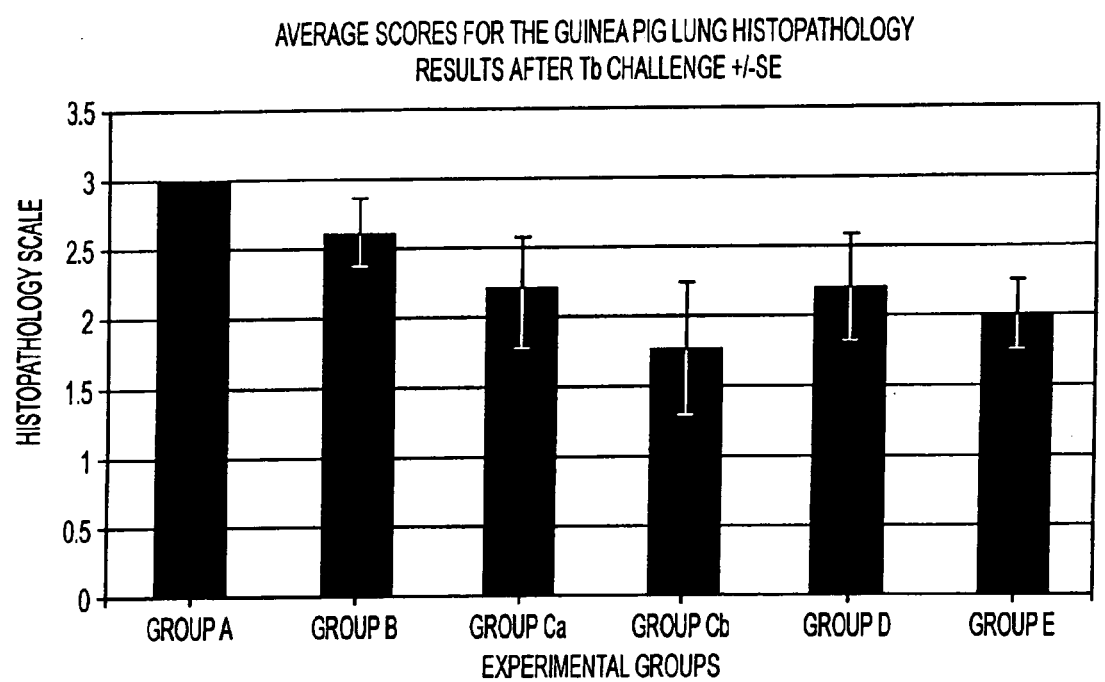
Figure 13B:
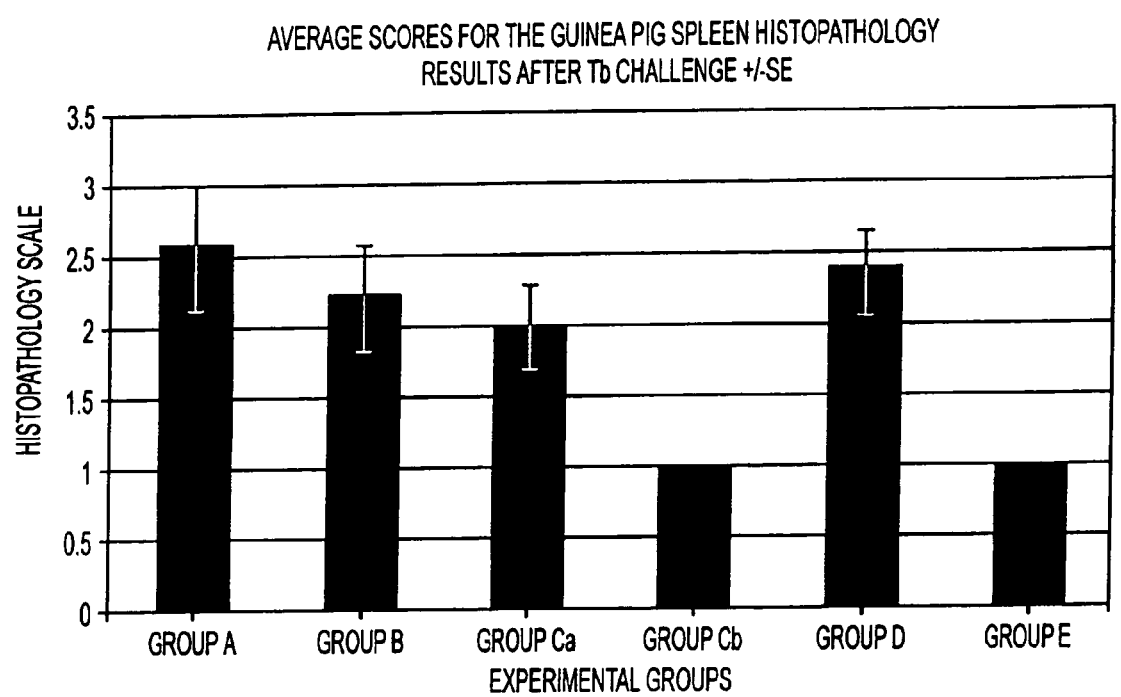

FIGS. 11A and 11B depict the bacillary load in the lungs and the spleens in the guinea pigs five weeks post challenge. The bars represent the geometric mean titers in the lungs and the spleens while the symbols represent individual titers for each guinea pig in each group.

Histopathology

Histopathology was conducted on both lung and spleen samples. H+E and AFB (Acid Fast Bacteria, such as *M. tuberculosis*, maintain carbo fuchsin staining after acid decolorization) staining was examined.

Lung Histopathology

After three blind trials the lesions were separated into three groups and each animal (referred to by number), assigned to a group shown below in Table 1.

TABLE 1

Lung Lesions

| 1. Mild to moderate diffuse interstitial pneumonia with focal to multifocal granulomas. | 2. Moderate to severe multifocal to coalescing granulomatous pneumonia. | 3. Severe multifocal to coalescing necrotizing granulomatous pneumonia. |
|---|---|---|
| 410 | 401 | 403 |
| 422 | 407 | 405 |
| 439 | 413 | 412 |
| 450 | 415 | 416 |
| 458 | 424 | 417 |
|  | 426 | 427 |
|  | 446 | 430 |
|  | 454 | 432 |
|  | 456 | 438 |
|  | 459 | 441 |
|  |  | 442 |
|  |  | 444 |
|  |  | 451 |
|  |  | 453 |
| Number per group 5 | 10 | 14 |

Total = 29

Although such classifications are necessarily somewhat subjective, there is a recognizable difference between those in group 1 and those in group 3.

Spleen Histopathology

After three blind trials, spleen lesions in the animals (referred to by number) were classified as one of three groups, shown below in Table 2.

TABLE 2

Spleen Lesions

| 1. Mild to moderate lymphocytic splenitis. | 2. Moderate to severe granulomatous splenitis. | 3. Severe necrotizing granulomatous splenitis. |
|---|---|---|
| 410 | 407 | 401 |
| 412 | 415 | 403 |
| 413 | 417 | 405 |
| 416 | 426 | 427 |
| 422 | 430 | 438(B) |
| 424 | 441(B) | 444 |
| 432 | 450 | 451 |
| 439(B) | 453 | 454 |
| 442(B) |  | 459 |
| 446 |  |  |
| 456 |  |  |
| 458 |  |  |
| Number per group 12 | 8 | 9 |

Total = 29

(B)= Two or three spleen sections only.

Lesions in group 1 are characterized by increased lymphocytes around follicles, with a few macrophages. No germinal centers (characteristic of "reactive follicles") were seen. The contrast between group assignment in the splenic lesions is more marked than the lung lesions. AFB stained sections of lung and spleen were examined. Acid fast bacilli are rare except within necrotic foci, and are generally more prevalent in the lung. Table 3 shows individual histopathology scores for guinea pig lungs five weeks after challenge with *M. tuberculosis* (depicted as animal number/histopathology score).

TABLE 3

Lung Histopathology by Test Group

| Group A | Group B | Group Ca | Group Cb | Group D | Group E |
|---|---|---|---|---|---|
| 403/3 | 401/2 | *439/1 | *410/1 | 450/1 | 422/1 |
| *412/3 | 454/2 | 415/2 | 458/1 | 407/2 | *413/2 |
| 427/3 | *416/3 | 426/2 | 424/2 | 459/2 | 446/2 |
| 444/3 | 430/3 | 405/3 | *442/3 | 417/3 | 456/2 |
| 451/3 | 441/3 | 453/3 |  | 438/3 | 432/3 |

*Undetectable bacilli in the spleen

Table 4 shows individual histopathology scores for guinea pig spleens five weeks after challenge with *M. tuberculosis* (depicted as animal number/histopathology score).

TABLE 4

Spleen Histopathology by Test Group

| Group A | Group B | Group Ca | Group Cb | Group D | Group E |
|---|---|---|---|---|---|
| *412/1 | *416/1 | *439/1 | *410/1 | 407/2 | *413/1 |
| 403/3 | 430/2 | 415/2 | 424/1 | 417/2 | 422/1 |
| 427/3 | 441/2 | 426/2 | *442/1 | 450/2 | 432/1 |
| 444/3 | 401/3 | 453/2 | 458/1 | 438/3 | 446/1 |
| 451/3 | 454/3 | 405/3 |  | 459/3 | 456/1 |

*Undetectable bacilli in the spleen

Thus, although DNA immunization did not prevent growth of *M. tuberculosis* in the lungs of guinea pigs, 20–25% of the guinea pigs were protected from dissemination of bacilli from the lungs to the spleen. Immunization using particle-mediated delivery techniques was also shown to be more efficient than intramuscular (IM) immunization.

In particular, the particle-mediated delivery device used only 5 μg DNA per immunization (a total of three immunizations), while IM administration (U.S. Pat. No. 5,736,524) required 400 μg of DNA per immunization (total of three immunizations). Moreover, immunization by particle-mediated delivery techniques showed a >1-log reduction in spleen bacterial counts relative to IM immunization.

Survival/Weight Loss Studies

FIG. 12, panels A–F depict survival/weight loss studies (weight loss greater than 150 grams is usually associated with death) for guinea pigs challenged with *M. tuberculosis*. The final data point on each line indicates the day the guinea pig was euthanized. Results are also shown in Table 5:

TABLE 5

Survival Studies

| Group | Survival rate |
|---|---|
| A | 1/4 |
| B | 1/5 |
| Ca | 2/5 |
| Cb | 4/5 |
| D | 0/5 |
| E | 4/4 |

Thus, there does not appear to be an obvious correlation between the histopathology of lung and spleen lesions in individual animals. The data indicates that there is reduced pathology in the lungs and spleens in groups Cb (DNA prime/BCG boost) and E (BCG alone) relative to the naïve controls and Group Cb animals exhibit reduced pathology in the lungs relative to Group E animals. This correlates with the bacterial counts in the spleen data. In addition, histological studies indicate that particle-mediated delivery immunization of guinea pigs with an antigen 85 DNA vaccine (Group A) exacerbates the disease. In particular, lung histopathological five out of five test guinea pigs had severe damage to tissue (as indicated by a score of "3") while in the control group two out of five animals exhibited severe damage. Similarly, for spleen histopathology, four of five animals immunized with the 85A antigen exhibited severe damage while two of five control animals had severe damage to spleen tissue.

The histological evidence also indicates that immunization by priming with a DNA vaccine followed by a BCG boost was more effective than BCG immunization alone. Thus, priming immunizations with a DNA vaccine by a particle-mediated delivery device elicits the type of immune responses necessary for protection from *tuberculosis* challenge and that the *M. tuberculosis* DNA vaccine worked synergistically with the BCG vaccine. In contrast, priming with culture filtrate protein followed by a BCG boost does not increase the effectiveness of BCG and a BCG prime does not boost BCG.

Example 3

Five cohorts of 10 guinea pigs are immunized three times at monthly intervals and challenged with *M. tuberculosis* 4 weeks after the final immunization. The five groups are as follows: Group A (10 plasmid cocktail DNA vaccine alone); Group B (10 plasmid cocktail DNA vaccine prime with a BCG boost); Group C (10 plasmid cocktail DNA vaccine prime with a culture filtrate protein boost); Group D (positive control, BCG alone); Group E (negative control, empty plasmid). Five weeks after challenge all of the guinea pigs are sacrificed for lung and spleen bacterial load determination and histological analysis of the lungs and spleens, as described above.

Accordingly, novel recombinant nucleic acid molecules, compositions comprising those molecules, and nucleic acid immunization techniques have been described. Although preferred embodiments of the subject invention have been described in some detail, it is understood that obvious variations can be made without departing from the spirit and the scope of the invention as defined by the appended claims.

What is claimed is:

1. A method for eliciting an immune response against *M. tuberculosis* in a human subject, said method comprising:
   (a) obtaining a vector construct, wherein the vector construct comprises a recombinant polynucleotide comprising a plurality of sequences each encoding a *Mycobacterium tuberculosis* antigen and each operably linked to control sequences suitable for expression in the subject; and
   (b) administering said vector construct to the human subject whereby said antigens are expressed in the human subject at sufficient levels to elicit an immune response.

2. The method of claim 1, further comprising administering at least one secondary composition in a boosting step to said subject wherein the secondary composition contains one or more nucleic acid molecules encoding said plurality of *Mycobacterium tuberculosis* antigens, or the secondary composition contains said plurality of *Mycobacterium tuberculosis* antigens.

3. The method of claim 2, wherein the secondary composition comprises at least one culture filtrate protein antigen of *M. tuberculosis*.

4. The method of claim 2, wherein the secondary composition comprises at least one isolated subunit of a *M. tuberculosis* protein.

5. The method of claim 2, wherein the secondary composition comprises a live attenuated vaccine derived from a *Mycobacterium* species.

6. The method of claim 5, wherein the live attenuated vaccine is BCG.

7. A method for eliciting an immune response against *M. tuberculosis* in a human subject, said method comprising:
   (a) obtaining a composition containing a plurality of recombinant polynucleotides each comprising a sequence encoding a *Mycobacterium tuberculosis* antigen operably linked to control sequences suitable for expression in the subject; and
   (b) administering the composition to the human subject whereby each said antigen is expressed in the human subject at sufficient levels to elicit an immune response.

8. The method of claim 7, further comprising administering at least one secondary composition in a boosting step to said subject wherein the secondary composition contains nucleic acid molecules encoding said *Mycobacterium tuberculosis* antigen, or the secondary composition contains said *Mycobacterium tuberculosis* antigen.

9. The method of claim 8, wherein the secondary composition comprises at least one culture filtrate protein antigen of *M. tuberculosis*.

10. The method of claim 8, wherein the secondary composition comprises at least one isolated subunit of a *M. tuberculosis* protein.

11. The method of claim 8, wherein the secondary composition comprises a live attenuated vaccine derived from a *Mycobacterium* species.

12. The method of claim 11, wherein the live attenuated vaccine is BCG.

13. The method of claim 1 or claim 7, wherein the administering is transdermal administration.

14. A method for eliciting an immune response to *M. tuberculosis* in a human subject, said method comprising:
   (a) providing a core carrier with a vector construct, wherein the vector construct comprises a recombinant polynucleotide comprising a plurality of sequences each encoding a *Mycobacterium tuberculosis* antigen and each operably linked to control sequences suitable for expression in the subject; and
   (b) administering the coated core carrier to the human subject using a particle-mediated delivery technique, wherein the *M. tuberculosis* antigens are expressed in the human subject at sufficient levels to elicit an immune response.

15. The method of claim 14, wherein the core carrier has an average diameter of about 0.5 to about 5 µm and a density sufficient to allow delivery into the subject.

16. The method of claim 14, wherein the core carrier is comprised of a metal.

17. The method of claim 16, wherein the metal is gold.

18. The method of claim 14, wherein step (b) is repeated.

19. The method of claim 14, further comprising administering at least one secondary composition in a boosting step to said subject wherein the secondary composition contains one or more nucleic acid molecules encoding said plurality of *Mycobacterium tuberculosis* antigens, or the secondary composition contains said plurality of *Mycobacterium tuberculosis* antigens.

20. The method of claim 19, where in the secondary composition comprises at least one culture filtrate protein antigen of *M. tuberculosis*.

21. The method of claim 19, wherein the secondary composition comprises at least one isolated subunit of a *M. tuberculosis* protein.

22. The method of claim 19, wherein the secondary composition comprises a live attenuated vaccine derived from a *Mycobacterium* species.

23. The method of claim 22, wherein the live attenuated vaccine is BCG.

24. A method for eliciting an immune response to *M. tuberculosis* in a human subject, said method comprising:
   (a) providing a core carrier coated with a composition containing a plurality of recombinant polynucleotides each comprising a sequence encoding a *Mycobacterium tuberculosis* antigen operably linked to control sequences suitable for expression in the subject; and
   (b) administering the coated core carrier to the human subject using a particle-mediated delivery technique, wherein the *M. tuberculosis* antigens are expressed in the human subject at sufficient levels to elicit an immune response.

25. The method of claim 24, wherein the core carrier has an average diameter of about 0.5 to about 5 µm and a density sufficient to allow delivery into the subject.

26. The method of claim 24, wherein the core carrier is comprised of a metal.

27. The method of claim 26, wherein the metal is gold.

28. The method of claim 24, wherein step (b) is repeated.

29. The method of claim 24, further comprising administering at least one secondary composition in a boosting step to said subject wherein the secondary composition contains one or more nucleic acid molecules encoding said plurality of *Mycobacterium tuberculosis* antigens, or the secondary composition contains said plurality of *Mycobacterium tuberculosis* antigens.

30. The method of claim 29, wherein the secondary composition comprises at least one culture filtrate protein antigen of *M. tuberculosis*.

31. The method of claim 29, wherein the secondary composition comprises at least one isolated subunit of a *M. tuberculosis* protein.

32. The method of claim 29, wherein the secondary composition comprises a live attenuated vaccine derived from a *Mycobacterium* species.

33. The method of claim 32, wherein the live attenuated vaccine is BCG.

* * * * *